United States Patent
Wisbey et al.

(10) Patent No.: US 9,622,685 B2
(45) Date of Patent: Apr. 18, 2017

(54) SYSTEM AND METHOD FOR PROVIDING A TRAINING LOAD SCHEDULE FOR PEAK PERFORMANCE POSITIONING USING EARPHONES WITH BIOMETRIC SENSORS

(71) Applicant: LOGITECH EUROPE, S.A., Lausanne (CH)

(72) Inventors: Ben Wisbey, Canberra (AU); David Shepherd, Canberra (AU); Stephen Duddy, Moama (AU)

(73) Assignee: LOGITECH EUROPE, S.A., Lausanne (CH)

( * ) Notice: Subject to any disclaimer, the term of this patent is extended or adjusted under 35 U.S.C. 154(b) by 5 days.

(21) Appl. No.: 14/871,992

(22) Filed: Sep. 30, 2015

(65) Prior Publication Data
US 2016/0023047 A1    Jan. 28, 2016

Related U.S. Application Data

(63) Continuation-in-part of application No. 14/830,549, filed on Aug. 19, 2015, which is a (Continued)

(51) Int. Cl.
*A63B 24/00* (2006.01)
*A61B 5/11* (2006.01)
(Continued)

(52) U.S. Cl.
CPC .......... *A61B 5/1118* (2013.01); *A61B 5/0205* (2013.01); *A61B 5/02427* (2013.01);
(Continued)

(58) Field of Classification Search
CPC ... A63B 24/00; A63B 24/0062; A61B 5/1118; A61B 5/02427; A61B 5/0205; A61B 5/6898; A61B 5/6817; G09B 23/288
See application file for complete search history.

(56) References Cited

U.S. PATENT DOCUMENTS 2,189,096 A    2/1940   Alonge
3,543,724 A    12/1970  Kirkpatrick et al.
(Continued)

OTHER PUBLICATIONS

"Elite Clock Military Style LED Watch" by ledwatchsuk. YouTube [dated May 31, 2011][online][retrieved on Aug. 14, 2015].
(Continued)

*Primary Examiner* — Glenn Richman
(74) *Attorney, Agent, or Firm* — Patterson & Sheridan, LLP

(57) ABSTRACT

Systems and methods are disclosed for providing a user a training load schedule for peak performance using earphones with biometric sensors. In one embodiment, the system includes earphones, including: speakers; a processor; a heartrate sensor electrically coupled to the processor; and a motion sensor electrically coupled to the processor. In this embodiment, the system also includes a memory coupled to a processor and having instructions stored that, when executed by the processor: display on a display an initial load schedule stored in a memory to the user; calculate a fatigue level of the user based on signals generated by the heartrate sensor; modify the initial load schedule based on the calculated fatigue level to create a dynamic load schedule for the user; and display on the display the dynamic load schedule to the user.

21 Claims, 19 Drawing Sheets

Related U.S. Application Data continuation-in-part of application No. 14/142,633, filed on Dec. 27, 2013, now Pat. No. 9,314,172, which is a continuation-in-part of application No. 14/140,414, filed on Dec. 24, 2013, which is a continuation-in-part of application No. 14/137,942, filed on Dec. 20, 2013, which is a continuation-in-part of application No. 14/137,734, filed on Dec. 20, 2013, which is a continuation-in-part of application No. 14/062,815, filed on Oct. 24, 2013.

(51) Int. Cl.
  *G09B 19/00* (2006.01)
  *A61B 5/024* (2006.01)
  *A61B 5/0205* (2006.01)
  *A61B 5/00* (2006.01)
  *G09B 23/28* (2006.01)

(52) U.S. Cl.
  CPC .......... *A61B 5/6817* (2013.01); *A61B 5/6898* (2013.01); *G09B 19/0038* (2013.01); *G09B 23/288* (2013.01)

(56) References Cited

U.S. PATENT DOCUMENTS

| | | |
|---|---|---|
| 3,978,849 A | 9/1976 | Geneen |
| 4,129,124 A | 12/1978 | Thalmann |
| 4,224,948 A | 9/1980 | Cramer et al. |
| 4,307,727 A | 12/1981 | Haynes |
| 4,331,154 A | 5/1982 | Broadwater et al. |
| 4,407,295 A | 10/1983 | Steuer et al. |
| 4,409,983 A | 10/1983 | Albert |
| 4,491,970 A | 1/1985 | LaWhite et al. |
| 5,301,154 A | 4/1994 | Suga |
| 5,392,261 A | 2/1995 | Hsu |
| 5,406,952 A | 4/1995 | Barnes et al. |
| 5,524,637 A | 6/1996 | Erickson |
| 5,734,625 A | 3/1998 | Kondo |
| 5,755,623 A | 5/1998 | Mizenko |
| 5,899,370 A | 5/1999 | Bould |
| 6,151,968 A | 11/2000 | Chou |
| 6,361,503 B1 | 3/2002 | Starobin et al. |
| 6,736,759 B1 | 5/2004 | Stubbs et al. |
| 7,192,401 B2 | 3/2007 | Saalasti et al. |
| 7,717,827 B2 | 5/2010 | Kurunmaki et al. |
| 7,914,425 B2 | 3/2011 | Hanoun |
| 8,992,385 B2 | 3/2015 | Lemos |
| 2002/0151811 A1 | 10/2002 | Starobin et al. |
| 2002/0188210 A1 | 12/2002 | Aizawa |
| 2003/0065269 A1 | 4/2003 | Vetter et al. |
| 2005/0056655 A1 | 3/2005 | Gary |
| 2005/0116811 A1 | 6/2005 | Eros et al. |
| 2005/0256416 A1 | 11/2005 | Chen |
| 2006/0183980 A1 | 8/2006 | Yang |
| 2007/0118043 A1 | 5/2007 | Oliver et al. |
| 2008/0086318 A1 | 4/2008 | Gilley et al. |
| 2008/0132383 A1 | 6/2008 | Einav et al. |
| 2008/0228089 A1 | 9/2008 | Cho et al. |
| 2009/0312656 A1 | 12/2009 | Lau et al. |
| 2010/0197463 A1 | 8/2010 | Haughay, Jr. et al. |
| 2011/0021319 A1 | 1/2011 | Nissila et al. |
| 2011/0092790 A1 | 4/2011 | Wilder-Smith et al. |
| 2011/0260870 A1 | 10/2011 | Bailey |
| 2012/0022341 A1 | 1/2012 | Zdeblick |
| 2012/0168471 A1 | 7/2012 | Wilson |
| 2012/0253485 A1 | 10/2012 | Weast et al. |
| 2013/0064049 A1 | 3/2013 | Pileri et al. |
| 2013/0237778 A1 | 9/2013 | Rouquette |
| 2014/0032234 A1 | 1/2014 | Anderson |
| 2014/0073486 A1 | 3/2014 | Ahmed et al. |
| 2014/0107493 A1 | 4/2014 | Yuen et al. |
| 2014/0228175 A1 | 8/2014 | Lemos et al. |

OTHER PUBLICATIONS

"Watch Stylish Blue Light LED Round Dial Matrix Stainless from ChinaBuye.com" by YnopoB. YouTube [dated Apr. 23, 2012][online][retrieved on Dec. 31, 2015] (https://www.youtube.com/watch?v=e_LWbXHvvWg).

SYSTEM AND METHOD FOR PROVIDING A TRAINING LOAD SCHEDULE FOR PEAK PERFORMANCE POSITIONING USING EARPHONES WITH BIOMETRIC SENSORS

CROSS-REFERENCE TO RELATED APPLICATIONS

This application is a continuation-in-part of and claims the benefit of U.S. patent application Ser. No. 14/830,549 filed Aug. 19, 2015, titled "Earphones with Biometric Sensors," the contents of which are incorporated herein by reference in their entirety. This application is also a continuation-in-part of and claims the benefit of U.S. patent application Ser. No. 14/142,633 filed Dec. 27, 2013, titled "System and Method for Providing a Training Load Schedule for Peak Performance Positioning," which is a continuation-in-part of U.S. patent application Ser. No. 14/140,414 filed Dec. 24, 2013, titled "System and Method for Providing an Intelligent Goal Recommendation for Activity Level," which is a continuation-in-part of U.S. patent application Ser. No. 14/137,942, filed Dec. 20, 2013, titled "System and Method for Providing an Interpreted Recovery Score," which is a continuation-in-part of and claims the benefit of U.S. patent application Ser. No. 14/137,734, filed Dec. 20, 2013, titled "System and Method for Providing a Smart Activity Score," which is a continuation-in-part of U.S. patent application Ser. No. 14/062,815, filed Oct. 24, 2013, titled "Wristband with Removable Activity Monitoring Device," the contents all of which are incorporated herein by reference in their entirety.

TECHNICAL FIELD

The present disclosure relates to earphones with biometric sensors, and more particularly embodiments describe a systems and methods for providing a user a training load schedule using earphones with biometric sensors.

BRIEF SUMMARY OF THE DISCLOSURE

According to embodiments of the technology disclosed herein, systems and methods are described for providing a user a training load schedule for peak performance positioning using earphones with biometric sensors.

In one embodiment, a system for providing a user a training load schedule, includes: a pair of earphones, including: speakers; a processor; a heartrate sensor electrically coupled to processor; and a motion sensor electrically coupled to the processor, where the processor is configured to process electronic input signals from the motion sensor and the heartrate sensor. In this embodiment, the system is configured to: display an initial load schedule to the user; calculate a fatigue level of the user based on signals generated by the heartrate sensor; modify the initial load schedule based on the calculated fatigue level to create a dynamic load schedule for the user; and display the dynamic load schedule to the user. In various implementations of this embodiment, the system calculates a heart rate variability based on signals received from the heartrate sensor, and the fatigue level is calculated based on the calculated heart rate variability.

The dynamic load schedule in various implementations may be used by a user to prepare for an event that takes place on a future date. For example, the user's fatigue level may be detected every day to update the dynamic load schedule on a daily basis. In this manner, a user may be positioned for optimal performance on a specified date of an event.

In some embodiments, the displayed initial load schedule and dynamic load schedule include at least one of a recommended daily activity level and a recommended fatigue level. In implementations of these embodiments, the initial load schedule and the dynamic load schedule are displayed on a calendar using at least one of a color-coding representation and a numerical representation.

In some embodiments, the system: calculates a second fatigue level of the user based on signals generated by the heart rate sensor; modifies the dynamic load schedule based on the second fatigue level; and displays the modified dynamic load schedule to the user.

In some embodiments, the system receives an external dynamic load schedule; compares the dynamic load schedule to the external dynamic load schedule; and displays the comparison of the dynamic load schedule to the external dynamic load schedule. In some implementations of these embodiments, the external dynamic load schedule is associated with a second user. In other implementations of these embodiments, the external dynamic load schedule is a past dynamic load schedule of the user that is associated with a past event.

In further embodiments, the system determines if the user complies with the dynamic load schedule by monitoring a movement of the user based on electrical signals generated by a motion sensor of the earphones.

In a particular embodiment, the heartrate sensor is an optical heartrate sensor protruding from a side of the earphone proximal to an interior side of a user's ear when the earphone is worn. In implementations of this embodiment, the optical heartrate sensor is configured to measure the user's blood flow and to output an electrical signal representative of this measurement to the earphones processor.

Other features and aspects of the disclosed method and system will become apparent from the following detailed description, taken in conjunction with the accompanying drawings, which illustrate, by way of example, the features in accordance with embodiments of the disclosure. The summary is not intended to limit the scope of the claimed disclosure, which is defined solely by the claims attached hereto.

BRIEF DESCRIPTION OF THE DRAWINGS

The present disclosure, in accordance with one or more various embodiments, is described in detail with reference to the following Figures. The Figures are provided for purposes of illustration only and merely depict typical or example embodiments of the disclosure.

DETAILED DESCRIPTION

Previous generation fitness tracking devices generally enabled only a tracking of activity that accounts for total calories burned. Currently available fitness tracking devices now add functionality that provides universal metabolic equivalent tasks in attempt to guide a user's training schedule for an upcoming event. One issue is that currently available fitness tracking devices do not account for the performance state, or recovery state (or fatigue level), of the user in a scientific, user-specific way to provide the user with a training load schedule that will position the user in an optimal performance, or recovery zone, on the day of a scheduled, future event. Another issue is that currently available solutions do not dynamically update the training load schedule in response to measuring the user's actual fatigue (or recovery) levels on an ongoing basis.

In view of the above drawbacks, there exists a long-felt need for fitness monitoring devices that detect a fatigue level in a scientific way and provide a user-specific training load schedule that is dynamically updated based on periodic detection of the fatigue level. Further, there is a need for fitness monitoring devices that incorporate this dynamically updated load schedule to prepare a user for an event to take place on a specified date.

The present disclosure addresses the aforementioned issues and is directed toward systems and methods for providing a training load schedule for peak performance positioning. In particular embodiments, the systems and methods are directed to earphones with biometric sensors that are used to provide a training load schedule.

Figure 1:
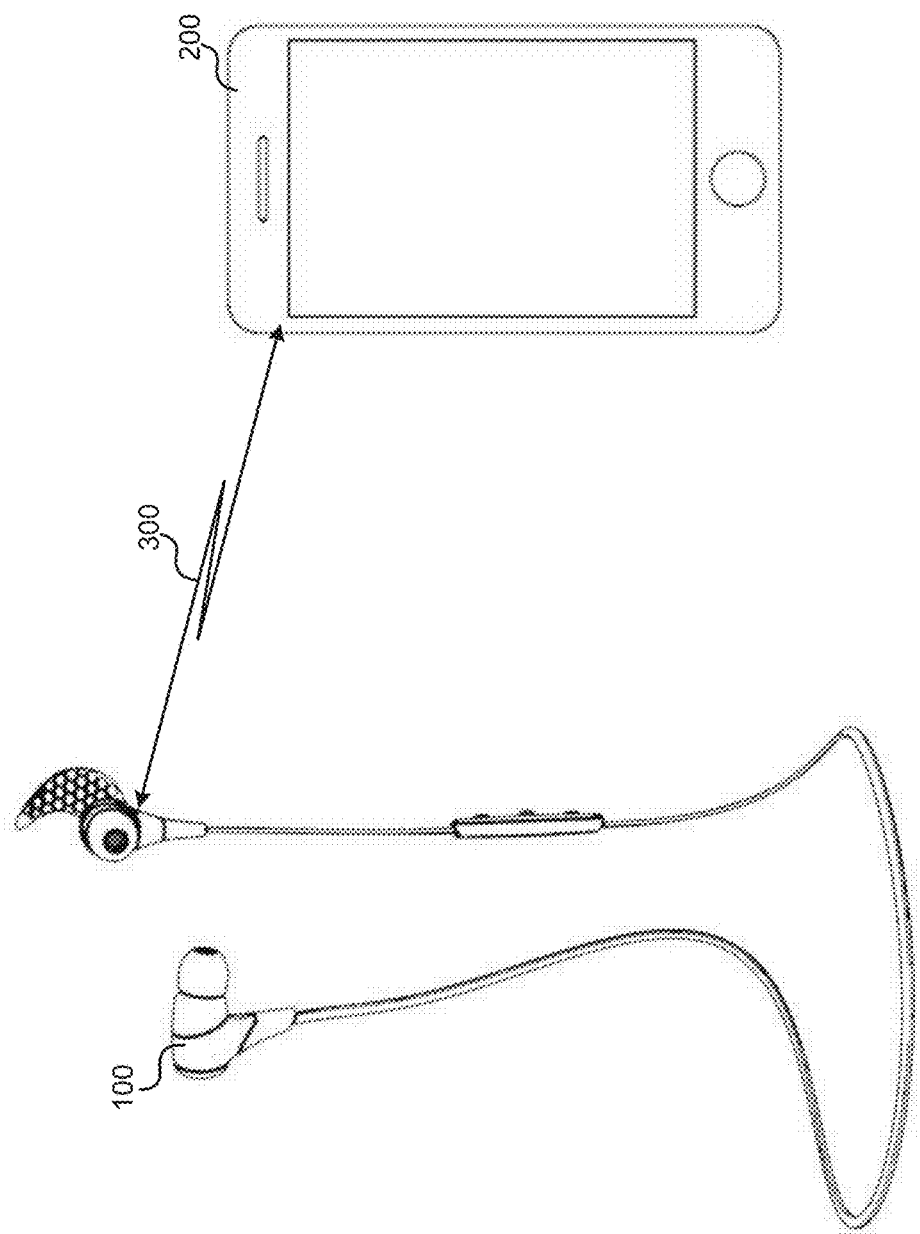
FIG. 1 illustrates an example communications environment in which embodiments of the disclosed technology may be implemented.

FIG. 1 illustrates an example communications environment in accordance with an embodiment of the technology disclosed herein. In this embodiment, earphones 100 communicate biometric and audio data with computing device 200 over a communication link 300. The biometric data is measured by one or more sensors (e.g., heart rate sensor, accelerometer, gyroscope) of earphones 100. Although a smartphone is illustrated, computing device 200 may comprise any computing device (smartphone, tablet, laptop, smartwatch, desktop, etc.) configured to transmit audio data to earphones 100, receive biometric data from earphones 100 (e.g., heartrate and motion data), and process the biometric data collected by earphones 100. In additional embodiments, computing device 200 itself may collect additional biometric information that is provided for display. For example, if computing device 200 is a smartphone it may use built in accelerometers, gyroscopes, and a GPS to collect additional biometric data.

Computing device 200 additionally includes a graphical user interface (GUI) to perform functions such as accepting user input and displaying processed biometric data to the user. The GUI may be provided by various operating systems known in the art, such as, for example, iOS, Android, Windows Mobile, Windows, Mac OS, Chrome OS, Linux, Unix, a gaming platform OS, etc. The biometric information displayed to the user can include, for example a summary of the user's activities, a summary of the user's fitness levels, activity recommendations for the day, the user's heart rate and heart rate variability (HRV), and other activity related information. User input that can be accepted on the GUI can include inputs for interacting with an activity tracking application further described below.

In preferred embodiments, the communication link 300 is a wireless communication link based on one or more wireless communication protocols such as BLUETOOTH, ZIGBEE, 802.11 protocols, Infrared (IR), Radio Frequency (RF), etc. Alternatively, the communications link 300 may be a wired link (e.g., using any one or a combination of an audio cable, a USB cable, etc.)

Figure 2A:
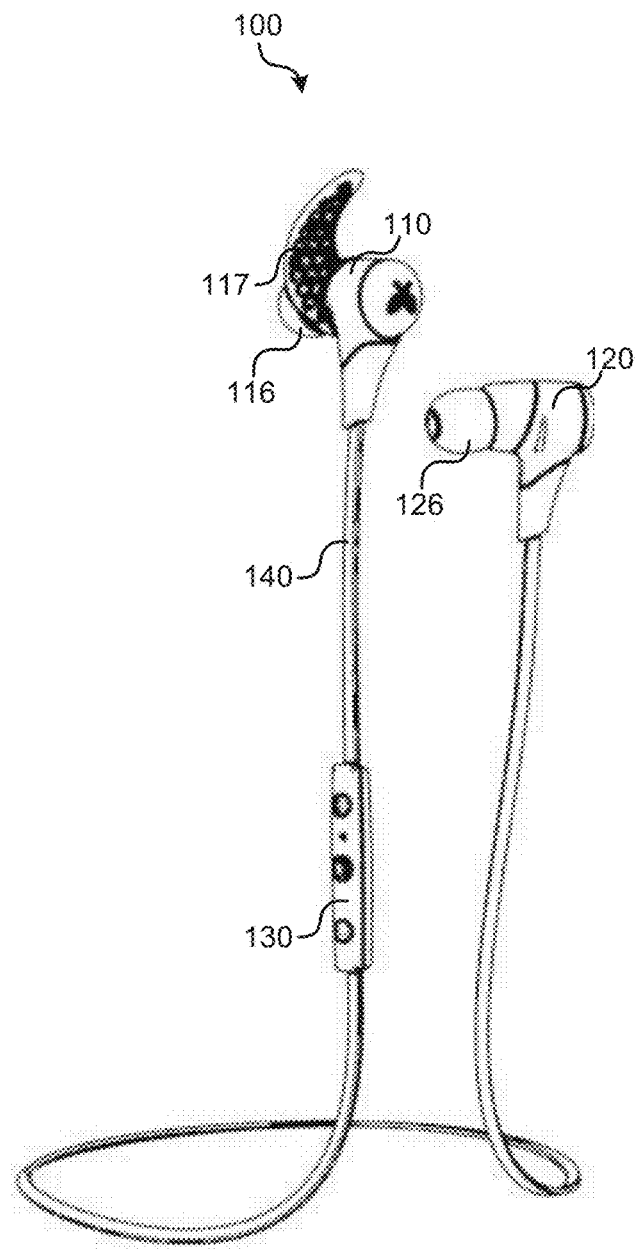
FIG. 2A illustrates a perspective view of exemplary earphones that may be used to implement the technology disclosed herein.

With specific reference now to earphones 100, FIG. 2A is a diagram illustrating a perspective view of exemplary earphones 100. FIG. 2A will be described in conjunction with FIG. 2B, which is a diagram illustrating an example architecture for circuitry of earphones 100. Earphones 100 comprise a left earphone 110 with tip 116, a right earphone 120 with tip 126, a controller 130 and a cable 140. Cable 140 electrically couples the right earphone 110 to the left earphone 120, and both earphones 110-120 to controller 130. Additionally, each earphone may optionally include a fin or ear cushion 117 that contacts folds in the outer ear anatomy to further secure the earphone to the wearer's ear.

In embodiments, earphones 100 may be constructed with different dimensions, including different diameters, widths, and thicknesses, in order to accommodate different human ear sizes and different preferences. In some embodiments of earphones 100, the housing of each earphone 110, 120 is rigid shell that surrounds electronic components. For example, the electronic components may include motion sensor 121, optical heartrate sensor 122, audio-electronic components such as drivers 113, 123 and speakers 114, 124, and other circuitry (e.g., processors 160, 165, and memories 170, 175). The rigid shell may be made with plastic, metal, rubber, or other materials known in the art. The housing may be cubic shaped, prism shaped, tubular shaped, cylindrical shaped, or otherwise shaped to house the electronic components.

The tips 116, 126 may be shaped to be rounded, parabolic, and/or semi-spherical, such that it comfortably and securely fits within a wearer's ear, with the distal end of the tip contacting an outer rim of the wearer's outer ear canal. In some embodiments, the tip may be removable such that it may be exchanged with alternate tips of varying dimensions, colors, or designs to accommodate a wearer's preference and/or fit more closely match the radial profile of the wearer's outer ear canal. The tip may be made with softer materials such as rubber, silicone, fabric, or other materials as would be appreciated by one of ordinary skill in the art.

In embodiments, controller 130 may provide various controls (e.g., buttons and switches) related to audio playback, such as, for example, volume adjustment, track skipping, audio track pausing, and the like. Additionally, controller 130 may include various controls related to biometric data gathering, such as, for example, controls for enabling or disabling heart rate and motion detection. In a particular embodiment, controller 130 may be a three button controller.

The circuitry of earphones 100 includes processors 160 and 165, memories 170 and 175, wireless transceiver 180, circuitry for earphone 110 and earphone 120, and a battery 190. In this embodiment, earphone 120 includes a motion sensor 121 (e.g., an accelerometer or gyroscope), an optical heartrate sensor 122, and a right speaker 124 and corresponding driver 123. Earphone 110 includes a left speaker 114 and corresponding driver 113. In additional embodiments, earphone 110 may also include a motion sensor (e.g., an accelerometer or gyroscope), and/or an optical heartrate sensor.

Figure 2B:
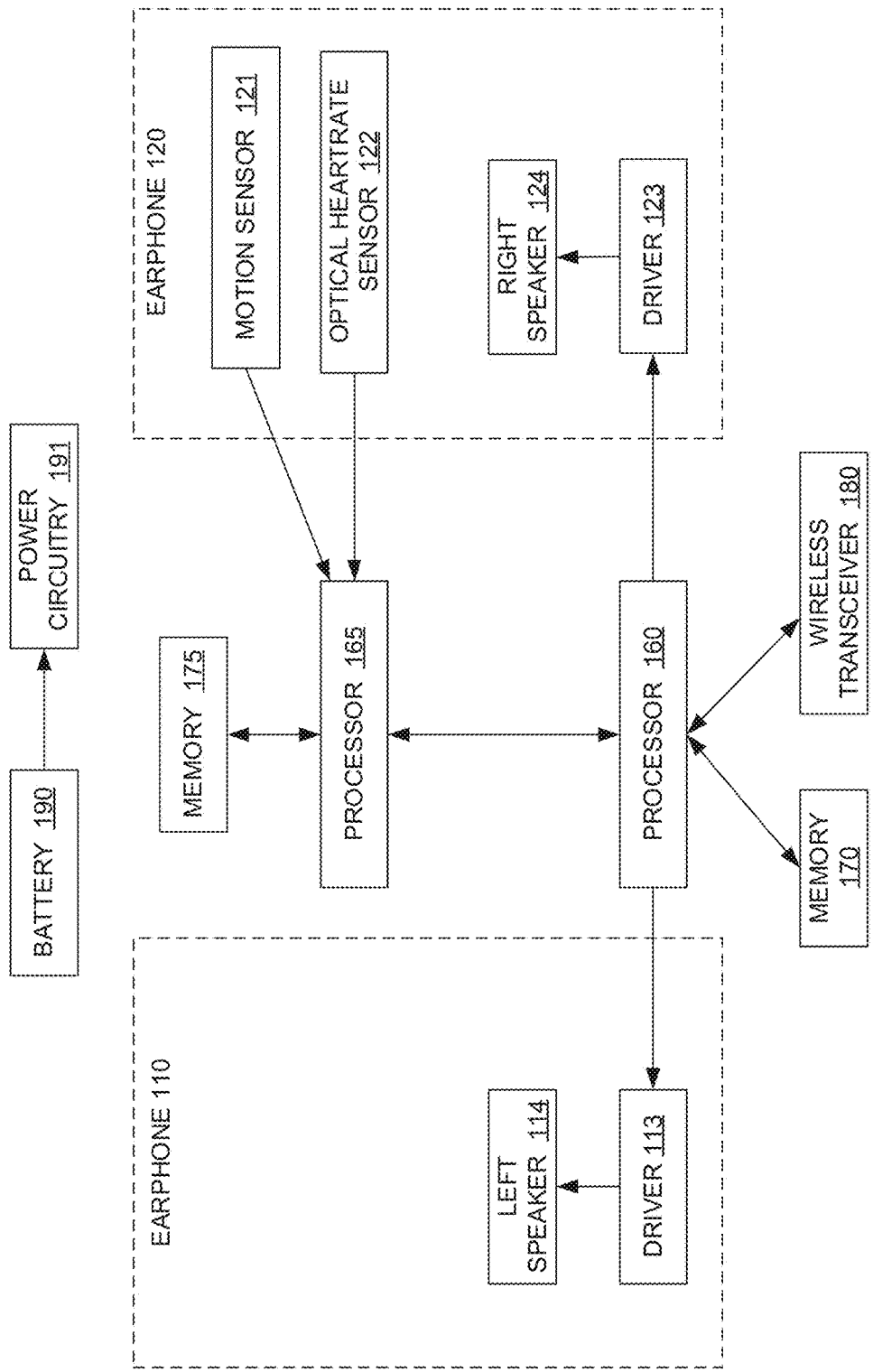
FIG. 2B illustrates an example architecture for circuitry of the earphones of FIG. 2A.

A biometric processor 165 comprises logical circuits dedicated to receiving, processing and storing biometric information collected by the biometric sensors of the earphones. More particularly, as illustrated in FIG. 2B, processor 165 is electrically coupled to motion sensor 121 and optical heartrate sensor 122, and receives and processes electrical signals generated by these sensors. These processed electrical signals represent biometric information such as the earphone wearer's motion and heartrate. Processor 165 may store the processed signals as biometric data in memory 175, which may be subsequently made available to a computing device using wireless transceiver 180. In some embodiments, sufficient memory is provided to store biometric data for transmission to a computing device for further processing.

During operation, optical heartrate sensor 122 uses a photoplethysmogram (PPG) to optically obtain the user's heart rate. In one embodiment, optical heartrate sensor 122 includes a pulse oximeter that detects blood oxygenation level changes as changes in coloration at the surface of a user's skin. More particularly, in this embodiment, the optical heartrate sensor 122 illuminates the skin of the user's ear with a light-emitting diode (LED). The light penetrates through the epidermal layers of the skin to underlying blood vessels. A portion of the light is absorbed and a portion is reflected back. The light reflected back through the skin of the user's ear is then obtained with a receiver (e.g., a photodiode) and used to determine changes in the user's blood oxygen saturation (SpO2) and pulse rate, thereby permitting calculation of the user's heart rate using algorithms known in the art (e.g., using processor 165). In this embodiment, the optical sensor may be positioned on one of the earphones such that it is proximal to the interior side of a user's tragus when the earphones are worn.

In various embodiments, optical heartrate sensor 122 may also be used to estimate a heart rate variable (HRV), i.e. the variation in time interval between consecutive heartbeats, of the user of earphones 100. For example, processor 165 may calculate the HRV using the data collected by sensor 122 based on a time domain methods, frequency domain methods, and other methods known in the art that calculate HRV based on data such as the mean heart rate, the change in pulse rate over a time interval, and other data used in the art to estimate HRV.

In further embodiments, logic circuits of processor 165 may further detect, calculate, and store metrics such as the amount of physical activity, sleep, or rest over a period of time, or the amount of time without physical activity over a period of time. The logic circuits may use the HRV, the metrics, or some combination thereof to calculate a recovery score. In various embodiments, the recovery score may indicate the user's physical condition and aptitude for further physical activity for the current day. For example, the logic circuits may detect the amount of physical activity and the amount of sleep a user experienced over the last 48 hours, combine those metrics with the user's HRV, and calculate a recovery score. In various embodiments, the calculated recovery score may be based on any scale or range, such as, for example, a range between 1 and 10, a range between 1 and 100, or a range between 0% and 100%.

During audio playback, earphones 100 wirelessly receive audio data using wireless transceiver 180. The audio data is processed by logic circuits of audio processor 160 into electrical signals that are delivered to respective drivers 113 and 123 of left speaker 114 and right speaker 124 of earphones 110 and 120. The electrical signals are then converted to sound using the drivers. Any driver technologies known in the art or later developed may be used. For example, moving coil drivers, electrostatic drivers, electret drivers, orthodynamic drivers, and other transducer technologies may be used to generate playback sound.

The wireless transceiver 180 is configured to communicate biometric and audio data using available wireless communications standards. For example, in some embodiments, the wireless transceiver 180 may be a BLUETOOTH transmitter, a ZIGBEE transmitter, a Wi-Fi transmitter, a GPS transmitter, a cellular transmitter, or some combination thereof. Although FIG. 2B illustrates a single wireless transceiver 180 for both transmitting biometric data and receiving audio data, in an alternative embodiment, a transmitter dedicated to transmitting only biometric data to a computing device may be used. In this alternative embodiment, the transmitter may be a low energy transmitter such as a near field communications (NFC) transmitter or a BLUETOOTH low energy (LE) transmitter. In implementations of this particular embodiment, a separate wireless receiver may be provided for receiving high fidelity audio data from an audio source. In yet additional embodiments, a wired interface (e.g., micro-USB) may be used for communicating data stored in memories 165 and 175.

FIG. 2B also shows that the electrical components of headphones 100 are powered by a battery 190 coupled to power circuitry 191. Any suitable battery or power supply technologies known in the art or later developed may be used. For example, a lithium-ion battery, aluminum-ion battery, piezo or vibration energy harvesters, photovoltaic cells, or other like devices can be used. In embodiments, battery 190 may be enclosed in earphone 110 or earphone 120. Alternatively, battery 102 may be enclosed in controller 130. In embodiments, the circuitry may be configured to enter a low-power or inactive mode when earphones 100 are not in use. For example, mechanisms such as, for example, an on/off switch, a BLUETOOTH transmission disabling button, or the like may be provided on controller 130 such that a user may manually control the on/off state of power-consuming components of earphones 100.

It should be noted that in various embodiments, processors 160 and 165, memories 170 and 175, wireless transceiver 180, and battery 190 may be enclosed in and distributed throughout any one or more of earphone 110, earphone 120, and controller 130. For example, in one particular embodiment, processor 165 and memory 175 may be enclosed in earphone 120 along with optical heartrate sensor 122 and motion sensor 121. In this particular embodiment, these four components are electrically coupled to the same printed circuit board (PCB) enclosed in earphone 120. It should also be noted that although audio processor 160 and biometric processor 165 are illustrated in this exemplary embodiment as separate processors, in an alternative embodiment the functions of the two processors may be integrated into a single processor.

Figure 3A:
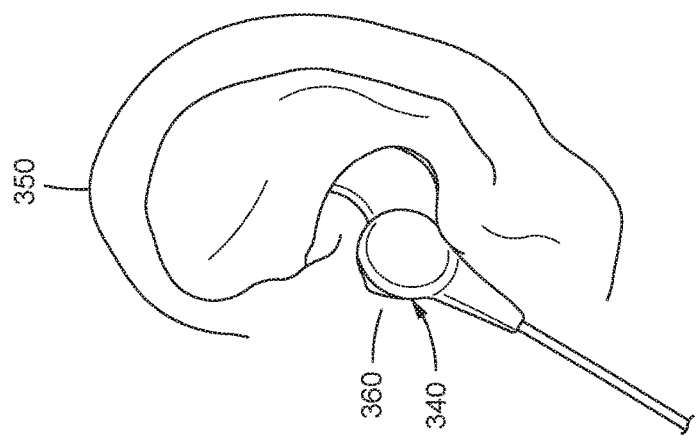
FIG. 3A illustrates a perspective view of a particular embodiment of an earphone, including an optical heartrate sensor, in accordance with the disclosed technology.
Figure 3B:
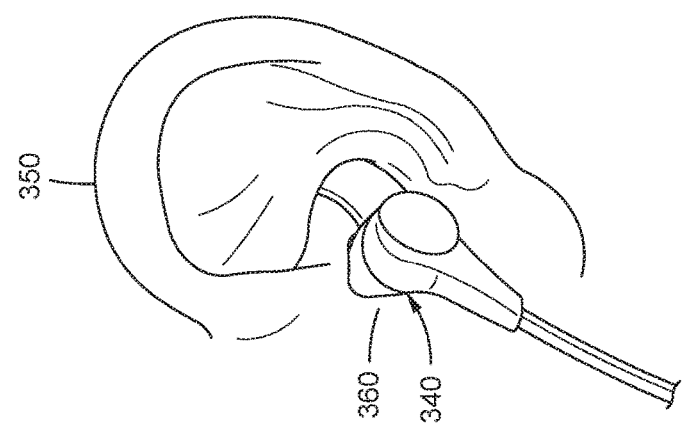
FIG. 3B illustrates a side perspective view of placement of the optical heartrate sensor of the earphones of FIG. 3A when they are worn by a user.
Figure 3C:
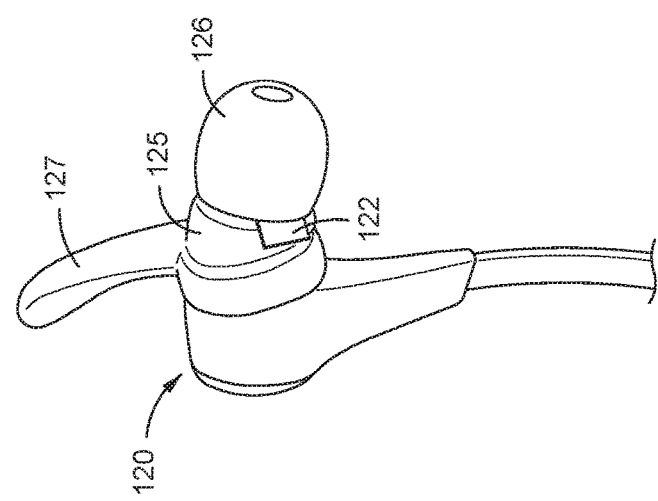
FIG. 3C illustrates a frontal perspective view of placement of the optical heartrate sensor of the earphones of FIG. 3A when they are worn by a user.

FIG. 3A illustrates a perspective view of one embodiment of an earphone 120, including an optical heartrate sensor 122, in accordance with the technology disclosed herein. FIG. 3A will be described in conjunction with FIGS. 3B-3C, which are perspective views illustrating placement of heartrate sensor 122 when earphone 120 is worn in a user's ear 350. As illustrated, earphone 120 includes a body 125, tip 126, ear cushion 127, and an optical heartrate sensor 122. Optical heartrate sensor 122 protrudes from a frontal side of body 125, proximal to tip 126 and where the earphone's nozzle (not shown) is present. FIGS. 3B-3C illustrate the optical sensor and ear interface 340 when earphone 120 is worn in a user's ear 350. When earphone 120 is worn, optical heartrate sensor 122 is proximal to the interior side of a user's tragus 360.

In this embodiment, optical heartrate sensor 122 illuminates the skin of the interior side of the ear's tragus 360 with a light-emitting diode (LED). The light penetrates through the epidermal layers of the skin to underlying blood vessels. A portion of the light is absorbed and a portion is reflected back. The light reflected back through the skin is then obtained with a receiver (e.g., a photodiode) of optical heartrate sensor 122 and used to determine changes in the user's blood flow, thereby permitting measurement of the user's heart rate and HRV.

In various embodiments, earphones 100 may be dual-fit earphones shaped to comfortably and securely be worn in either an over-the-ear configuration or an under-the-ear configuration. The secure fit provided by such embodiments keeps the optical heartrate sensor 122 in place on the interior side of the ear's tragus 360, thereby ensuring accurate and consistent measurements of a user's heartrate.

Figure 3F:
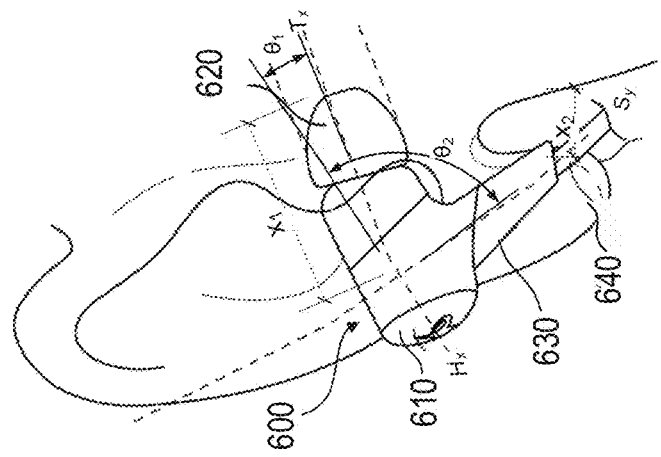
FIG. 3F illustrates a cross-sectional view of an under-the-ear configuration of the dual-fit earphones of FIG. 3D.
Figure 3E:
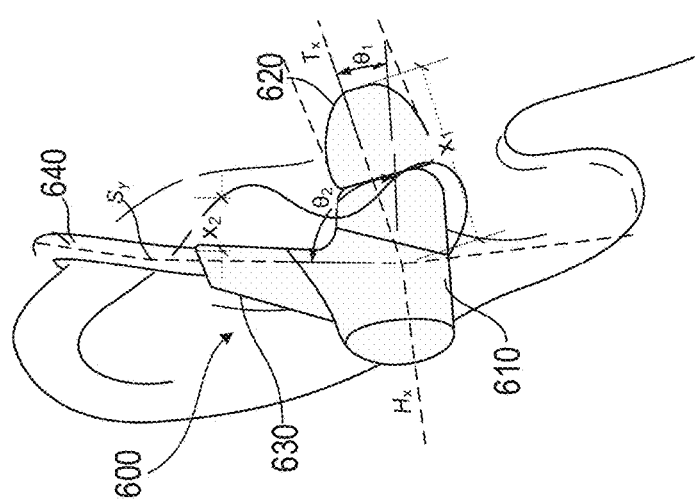
FIG. 3E illustrates a cross-sectional view of an over-the-ear configuration of the dual-fit earphones of FIG. 3D.
Figure 3D:
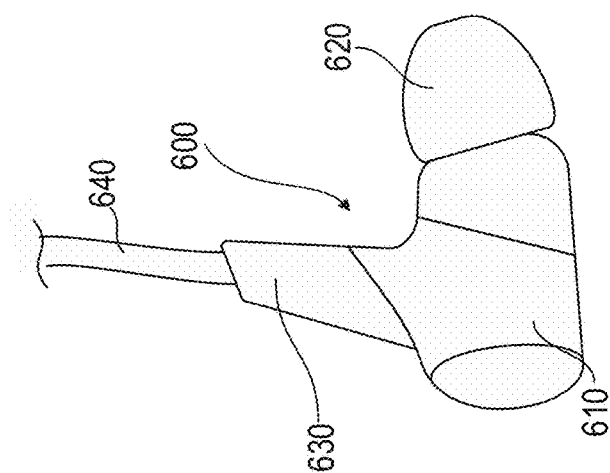
FIG. 3D illustrates a cross-sectional view of an over-the-ear configuration of dual-fit earphones in accordance with the disclosed technology.

FIGS. 3D and 3E are cross-sectional views illustrating one such embodiment of dual-fit earphones 600 being worn in an over-the-ear configuration. FIG. 3F illustrates dual-fit earphones 600 in an under-the-ear configuration.

As illustrated, earphone 600 includes housing 610, tip 620, strain relief 630, and cord or cable 640. The proximal end of tip 620 mechanically couples to the distal end of housing 610. Similarly, the distal end of strain relief 630 mechanically couples to a side (e.g., the top side) of housing 610. Furthermore, the distal end of cord 640 is disposed within and secured by the proximal end of strain relief 630. The longitudinal axis of the housing, $H_x$, forms angle $\theta_1$ with respect to the longitudinal axis of the tip, $T_x$. The longitudinal axis of the strain relief, $S_y$, aligns with the proximal end of strain relief 630 and forms angle $\theta_2$ with respect to the axis $H_x$. In several embodiments, $\theta_1$ is greater than 0 degrees (e.g., $T_x$ extends in a non-straight angle from $H_x$, or in other words, the tip 620 is angled with respect to the housing 610). In some embodiments, $\theta_1$ is selected to approximate the ear canal angle of the wearer. For example, $\theta_1$ may range between 5 degrees and 15 degrees. Also in several embodiments, $\theta_2$ is less than 90 degrees (e.g., $S_y$ extends in a non-orthogonal angle from $H_x$, or in other words, the strain relief 630 is angled with respect to a perpendicular orientation with housing 610). In some embodiments, $\theta_2$ may be selected to direct the distal end of cord 640 closer to the wearer's ear. For example, $\theta_2$ may range between 75 degrees and 89 degrees.

As illustrated, $x_1$ represents the distance between the distal end of tip 620 and the intersection of strain relief longitudinal axis $S_y$ and housing longitudinal axis $H_x$. One of skill in the art would appreciate that the dimension $x_1$ may be selected based on several parameters, including the desired fit to a wearer's ear based on the average human ear anatomical dimensions, the types and dimensions of electronic components (e.g., optical sensor, motion sensor, processor, memory, etc.) that must be disposed within the housing and the tip, and the specific placement of the optical sensor. In some examples, $x_1$ may be at least 18 mm. However, in other examples, $x_1$ may be smaller or greater based on the parameters discussed above.

Similarly, as illustrated, $x_2$ represents the distance between the proximal end of strain relief 630 and the surface wearer's ear. In the configuration illustrated, $\theta_2$ may be selected to reduce $x_2$, as well as to direct the cord 640 towards the wearer's ear, such that cord 640 may rest in the crevice formed where the top of the wearer's ear meets the side of the wearer's head. In some embodiments, $\theta_2$ may range between 75 degrees and 85 degrees. In some examples, strain relief 630 may be made of a flexible material such as rubber, silicone, or soft plastic such that it may be further bent towards the wearer's ear. Similarly, strain relief 630 may comprise a shape memory material such that it may be bent inward and retain the shape. In some examples, strain relief 630 may be shaped to curve inward towards the wearer's ear.

In some embodiments, the proximal end of tip 620 may flexibly couple to the distal end of housing 610, enabling a wearer to adjust $\theta_1$ to most closely accommodate the fit of tip 620 into the wearer's ear canal (e.g., by closely matching the ear canal angle).

Figure 4B:
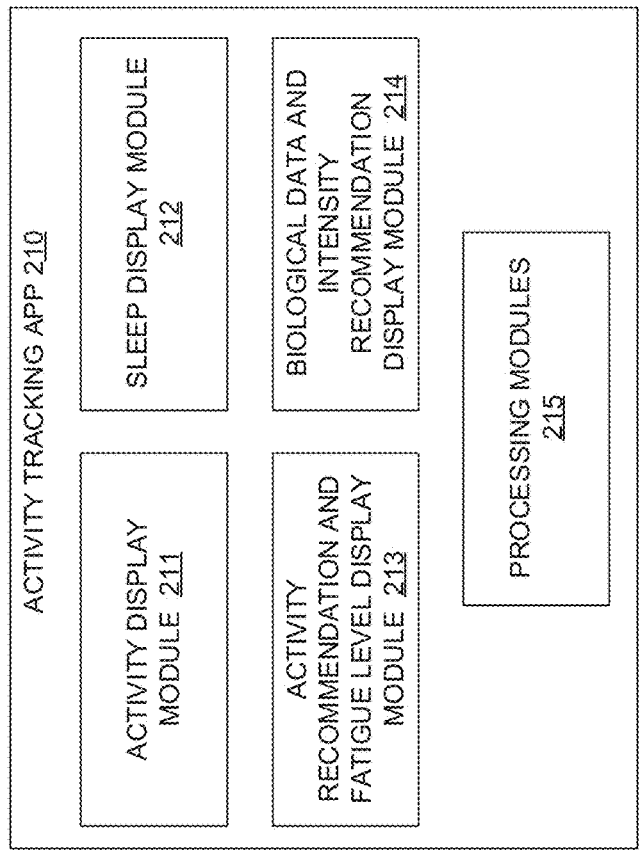
FIG. 4B illustrates modules of an example activity monitoring application that may be used to implement embodiments of the disclosed technology.
Figure 4A:
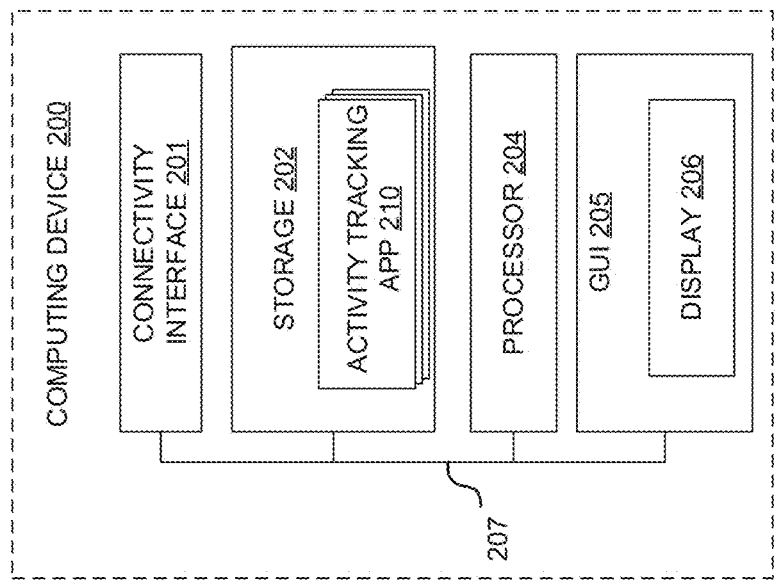
FIG. 4A is a block diagram illustrating an example computing device that may be used to implement embodiments of the disclosed technology.

As one having skill in the art would appreciate from the above description, earphones 100 in various embodiments may gather biometric user data that may be used to track a user's activities and activity level. That data may then be made available to a computing device, which may provide a GUI for interacting with the data using a software activity tracking application installed on the computing device. FIG. 4A is a block diagram illustrating example components of one such computing device 200 including an installed activity tracking application 210.

As illustrated in this example, computing device 200 comprises a connectivity interface 201, storage 202 with activity tracking application 210, processor 204, a graphical user interface (GUI) 205 including display 206, and a bus 207 for transferring data between the various components of computing device 200.

Connectivity interface 201 connects computing device 200 to earphones 100 through a communication medium. The medium may comprise a wireless network system such as a BLUETOOTH system, a ZIGBEE system, an Infrared (IR) system, a Radio Frequency (RF) system, a cellular network, a satellite network, a wireless local area network, or the like. The medium may additionally comprise a wired component such as a USB system.

Storage 202 may comprise volatile memory (e.g. RAM), non-volatile memory (e.g. flash storage), or some combination thereof. In various embodiments, storage 202 may store biometric data collected by earphones 100. Additionally, storage 202 stores an activity tracking application 210, that when executed by processor 204, allows a user to interact with the collected biometric information.

In various embodiments, a user may interact with activity tracking application 210 via a GUI 205 including a display 206, such as, for example, a touchscreen display that accepts various hand gestures as inputs. In accordance with various embodiments, activity tracking application 210 may process the biometric information collected by earphones 100 and present it via display 206 of GUI 205. Before describing activity tracking application 210 in further detail, it is worth noting that in some embodiments earphones 100 may filter the collected biometric information prior to transmitting the biometric information to computing device 200. Accordingly, although the embodiments disclosed herein are described with reference to activity tracking application 210 processing the received biometric information, in various implementations various preprocessing operations may be performed by a processor 160, 165 of earphones 100.

In various embodiments, activity tracking application 210 may be initially configured/setup (e.g., after installation on a smartphone) based on a user's self-reported biological information, sleep information, and activity preference information. For example, during setup a user may be prompted via display 206 for biological information such as the user's gender, height, age, and weight. Further, during setup the user may be prompted for sleep information such as the amount of sleep needed by the user and the user's regular bed time. Further, still, the user may be prompted during setup for a preferred activity level and activities the user desires to be tracked (e.g., running, walking, swimming, biking, etc.) In various embodiments, described below, this self-reported information may be used in tandem with the information collected by earphones 100 to display activity monitoring information using various modules.

Following setup, activity tracking application 210 may be used by a user to monitor and define how active the user wants to be on a day-to-day basis based on the biometric information (e.g., accelerometer information, optical heart rate sensor information, etc.) collected by earphones 100. As illustrated in FIG. 4B, activity tracking application 210 may comprise various display modules, including an activity display module 211, a sleep display module 212, an activity recommendation and fatigue level display module 213, and a biological data and intensity recommendation display module 214. Additionally, activity tracking application 210 may comprise various processing modules 215 for processing the activity monitoring information (e.g., optical heart-rate information, accelerometer information, gyroscope information, etc.) collected by the earphones or the biological information entered by the users. These modules may be implemented separately or in combination. For example, in some embodiments activity processing modules 215 may be directly integrated with one or more of display modules 211-214.

As will be further described below, each of display modules 211-214 may be associated with a unique display provided by activity tracking app 210 via display 206. That is, activity display module 211 may have an associated activity display, sleep display module 212 may have an associated sleep display, activity recommendation and fatigue level display module 213 may have an associated activity recommendation and fatigue level display, and biological data and intensity recommendation display module 214 may have an associated biological data and intensity recommendation display.

Figure 5:
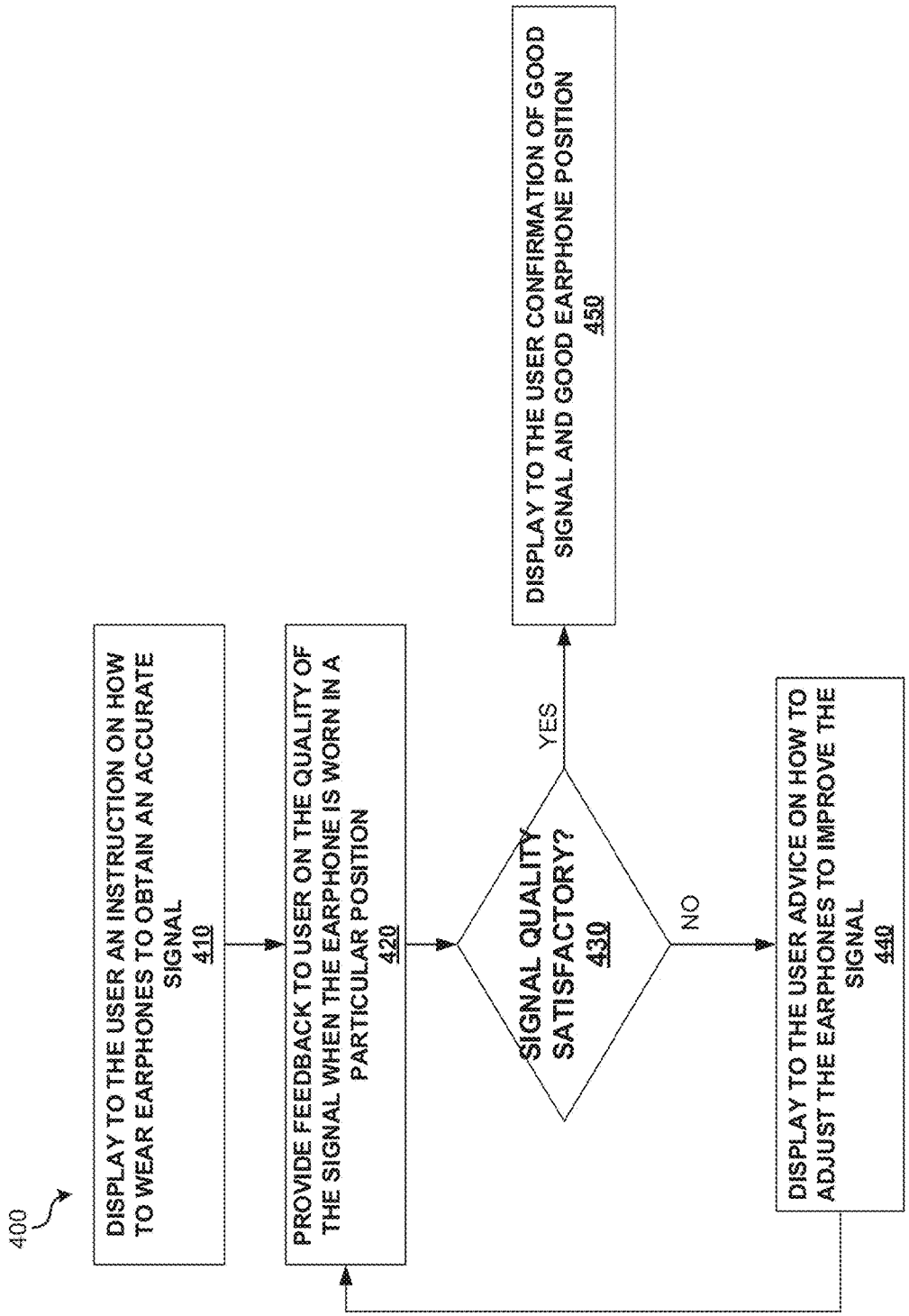
FIG. 5 is an operational flow diagram illustrating a method of prompting a user to adjust the placement of earphones in the user's ear to ensure accurate biometric data collection by the earphones' biometric sensors.

In embodiments, application 210 may be used to display to the user an instruction for wearing and/or adjusting earphones 100 if it is determined that optical heartrate sensor 122 and/or motion sensor 121 are not accurately gathering motion data and heart rate data. FIG. 5 is an operational flow diagram illustrating one such method 400 of an earphone adjustment feedback loop with a user that ensures accurate biometric data collection by earphones 100. At operation 410, execution of application 210 may cause display 206 to display an instruction to the user on how to wear earphones 100 to obtain an accurate and reliable signal from the biometric sensors. In embodiments, operation 410 may occur once after installing application 210, once a day (e.g., when user first wears the earphones 100 for the day), or at any customizable and/or predetermined interval.

At operation 420, feedback is displayed to the user regarding the quality of the signal received from the biometric sensors based on the particular position that earphones 100 are being worn. For example, display 206 may display a signal quality bar or other graphical element. At decision 430, it is determined if the biosensor signal quality is satisfactory for biometric data gathering and use of application 210. In various embodiments, this determination may be based on factors such as, for example, the frequency with which optical heartrate sensor 122 is collecting heart rate data, the variance in the measurements of optical heartrate sensor 122, dropouts in heart rate measurements by sensor 122, the signal-to-noise ratio approximation of optical heartrate sensor 122, the amplitude of the signals generated by the sensors, and the like.

If the signal quality is unsatisfactory, at operation 440, application 210 may cause display 206 to display to the user advice on how to adjust the earphones to improve the signal, and operations 420 and decision 430 may subsequently be repeated. For example, advice on adjusting the strain relief of the earphones may be displayed. Otherwise, if the signal quality is satisfactory, at operation 450, application may cause display 206 to display to the user confirmation of good signal quality and/or good earphone position. Subsequently, application 210 may proceed with normal operation (e.g., display modules 211-214).

Figure 6:
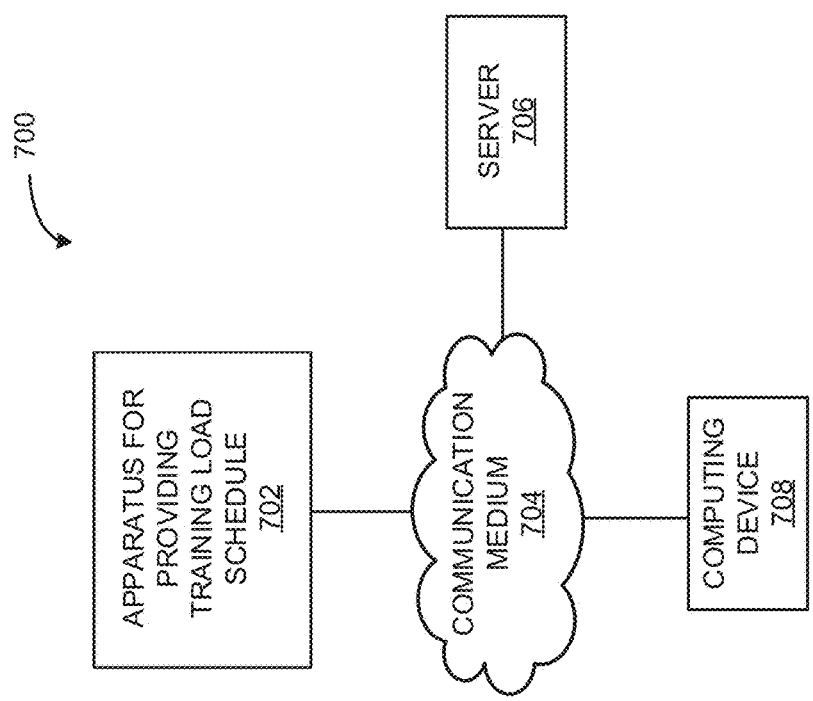
FIG. 6 illustrates an example system for providing a user a training load schedule.

In various embodiments, earphones 100 and computing device 200 may be implemented in a system for providing a training load schedule to the user. FIG. 6 is a schematic block diagram illustrating an example system 700 for providing a training load schedule to a user for peak performance. System 700 includes an apparatus for providing a training load schedule 702 (e.g., computing device 200), communication medium 704, server 706, and computing device 708 (e.g., earphones 100).

Communication medium 704 may be implemented in a variety of forms. For example, communication medium 704 may be an Internet connection, such as a local area network ("LAN"), a wide area network ("WAN"), a fiber optic network, internet over power lines, a hard-wired connection (e.g., a bus), and the like, or any other kind of network connection. Communication medium 704 may be implemented using any combination of routers, cables, modems, switches, fiber optics, wires, radio, and the like. Communication medium 704 may be implemented using various wireless standards, such as BLUETOOTH, Wi-Fi, LTE, etc.

Server 706 directs communications made over communication medium 704. Server 706 may be, for example, an Internet server, a router, a desktop or laptop computer, a smartphone, a tablet, a processor, a module, or the like. In one embodiment, server 706 directs communications between communication medium 704 and computing device 708. For example, server 706 may update information stored on computing device 708, or server 706 may send information to computing device 708 in real time.

Computing device 708 may take a variety of forms, such as a desktop or laptop computer, a smartphone, a tablet, a processor, a module, or the like. In addition, computing device 708 may be a module, processor, and/or other electronics embedded in a wearable device such as earphones, a bracelet, a smartwatch, a piece of clothing, and so forth. For example, computing device 708 may be substantially similar to electronics embedded in earphones 100. Computing device 708 may communicate with other devices over communication medium 704 with or without the use of server 706. In one embodiment, computing device 708 includes apparatus 702. In various embodiments, apparatus 702 may be used to perform various processes described herein.

Figure 7:
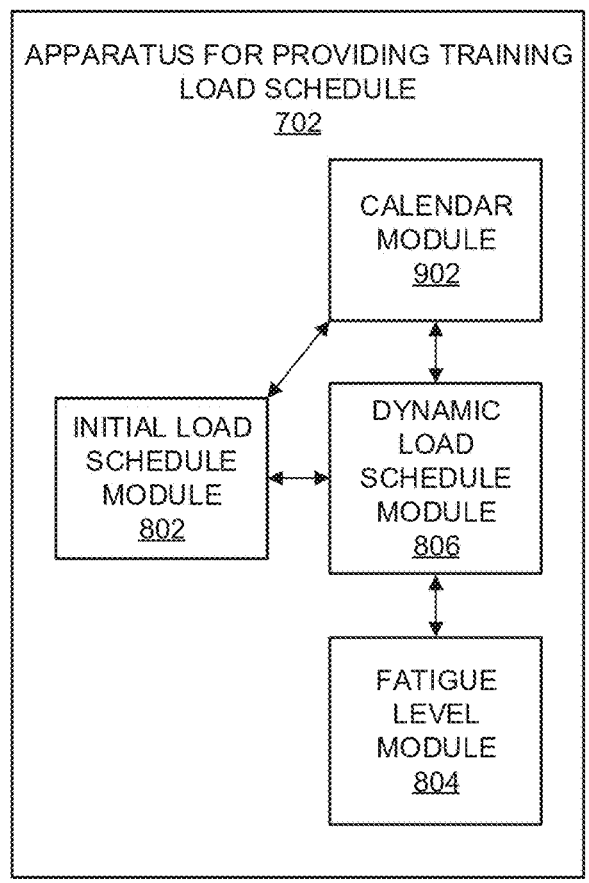
FIG. 7 illustrates an example apparatus for providing a user a training load schedule.

FIG. 7 is a schematic block diagram illustrating an embodiment of an apparatus 702 for providing a training load schedule. As illustrated in this particular embodiment, apparatus 702 includes initial load schedule module 802, fatigue level module 804, dynamic load schedule module 806, and calendar module 902. Initial load schedule module 802 provides an initial load schedule. Fatigue level module 804 detects a fatigue level. Dynamic load schedule module 806 creates and updates a dynamic load schedule by modifying the initial load schedule based on the fatigue level. Calendar module 902 maintains the dynamic load schedule and the initial load schedule. In a further embodiment, calendar module 902 displays at least one of the dynamic load schedule and the initial load schedule using a calendar and at least one of a color-coding representation and a numerical representation.

In addition, apparatus 702 may include a movement monitoring module (not shown) that monitors a user's movement to create a metabolic activity score based on the user's movement and user information. Initial load schedule module 802, fatigue level module 804, dynamic load schedule module 806, calendar module 902, and the movement monitoring module will be described below in further detail with regard to various processes.

In various embodiments, at least one of the movement monitoring module, initial load schedule module 802, fatigue level module 804, dynamic load schedule module 806, and calendar module 902 is embodied in earphones 100. In various embodiments, any of the modules described herein may be embodied in earphones 100 and connect to other modules described herein via communication medium 704.

Figure 8A:
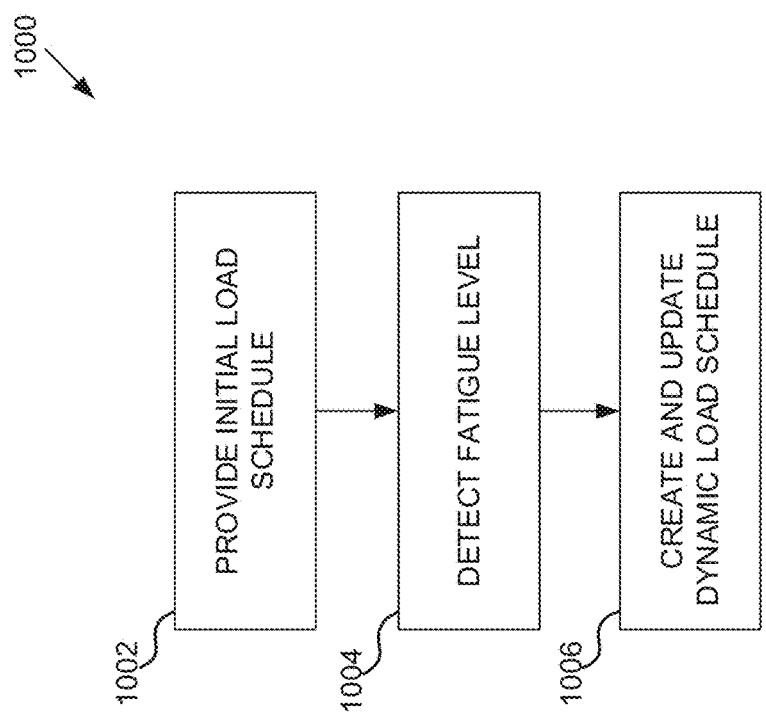
FIG. 8A is an operational flow diagram illustrating an example method for providing a user a training load schedule.

FIG. 8A is an operational flow diagram illustrating an example method 1000 for providing a training load schedule for peak performance positioning in accordance with an embodiment of the present disclosure. The operations of method 1000 create a dynamic load schedule based on detected fatigue level. This aids in preparing a user for a future event and in positioning the user in a peak performance zone based on the user's recovery and fatigue levels. In one embodiment, apparatus 702 and earphones 100 perform various operations of method 1000.

At operation 1002, an initial load schedule is provided to the user. For example, the initial load schedule may be displayed to the user on computing device 200 (e.g., using activity tracking application 210). The initial load schedule may take various forms. For example, the initial load schedule may include a target activity level for a user to achieve for a particular period of time (e.g., day, week, month). The initial load schedule may be uniform—i.e., constant over time periods—or may vary over time periods. In one embodiment, the initial load schedule includes a recommended daily activity level as tracked by a metabolic activity score, described in detail below. For example, the initial load schedule may include a recommended daily metabolic activity score of 2,000 points per day. In another embodiment, the initial load schedule includes a recommended fatigue level. The recommended fatigue level may be a fatigue level that a user attempts to achieve as a result of the user's activities. For example, the recommended fatigue level may be 60 points each day. In both of these embodiments, the initial load schedule is a metric to which a user may conform or attempt to conform.

In one embodiment, the initial load schedule is provided to the user based on normative data collected from a group of users. The normative data may provide a baseline initial load schedule that is not specific to the user. By way of example, the normative data may be based on publicly available data, or otherwise aggregated empirical data, related to training schedules for various events. One example of such normative data may include a popular training regimen for a marathon, broken down into training regimens, for beginning, average, and expert runners. One having skill in the art will appreciate the many variations possible with respect to the normative data that may be used to provide the initial load schedule.

In another embodiment, the initial load schedule is provided after detecting the user's fatigue level at least one time. In this embodiment, the fatigue level in combination with the normative data is used as a baseline for the initial load schedule. The initial load schedule, in one embodiment, is provided to prepare the user for an event to take place at a specified date. For example, the initial load schedule, if followed by the user, may prepare a user to run a marathon that is six months in the future. The initial load schedule module 802 provides the initial load schedule, in one embodiment, by determining the fitness level required for the event, creating a rough estimate of the user's current fitness level, and determining the amount of time until the event will take place. Based on the parameters, the initial load schedule can determine a baseline training schedule for the user.

In various embodiments of method 1000, the movement of the user may be monitored to determine a metabolic activity score based with the user's movement and user information. For example, the user's movement may be monitored using motion sensor 121 of earphones 100. The metabolic activity score may be determined from metabolic loadings. The metabolic loadings may be associated with the movement. In one embodiment, the metabolic loadings are determined by identifying a user activity type from a set of reference activity types and by identifying a user activity intensity from a set of reference activity intensities.

In one embodiment, the metabolic loadings may be determined based on information provided by a user (user information). User information may include, for example, an individual's height, weight, age, gender, geographic and environmental conditions, and the like. The user may provide the user information by, for example, a user interface of computing device 708 and/or apparatus 702 (e.g., using application 210 and GUI 205). User information may be determined based on various measurements—for example, measurements of the user's body-fat content or body type. In addition, the user information may be determined by an altimeter or GPS, which may be used to determine the user's elevation, weather conditions in the user's environment, etc. In one embodiment, apparatus 702 obtains user information from the user indirectly. For example, apparatus 702 may collect the user information from a social media account, from a digital profile, or the like.

The user information, in one embodiment, includes a user lifestyle selected from a set of reference lifestyles. For example, apparatus 702 may prompt the user for information about the user's lifestyle (e.g., via a user interface provided by application 210). By way of example, apparatus 702 may prompt the user to determine how active the user's lifestyle is. Additionally, the user may be prompted to select the user lifestyle from the set of reference lifestyles. The reference lifestyles may include a range of lifestyles, for example, ranging from inactive, on one end, to highly active on the other end. In such a case, the set of reference lifestyles may include sedentary, mildly active, moderately active, and heavily active.

In one instance, the user lifestyle is determined from the user as an initial matter. For example, upon initiation, apparatus 702 may prompt the user to provide the user lifestyle. In a further embodiment, the user is prompted periodically to select the user lifestyle. In this fashion, the user lifestyle selected may be aligned with the user's actual activity level as the user's activity level varies over time. In another embodiment, the user lifestyle is updated without intervention from the user.

In one embodiment, the metabolic loadings are numerical values and may represent a rate of calories burned per unit weight per unit time (e.g., having units of kcal per kilogram per hour). By way of example, the metabolic loadings may also be represented in units of oxygen uptake (e.g., in milliliters per kilogram per minute). In addition, the metabolic loadings may represent a ratio of the metabolic rate during activity (e.g., the metabolic rate associated with a particular activity type and/or activity intensity) to the metabolic rate during rest. The metabolic loadings, in one embodiment, are represented in a metabolic table, such as metabolic table 1050, illustrated in FIG. 8B. In one illustrative case, the metabolic loadings are specific to the user information. For example, the metabolic loadings may increase for a heavier user, or for an increased elevation, but may decrease for a lighter user or for a decreased elevation.

In one embodiment, the set of metabolic loadings is determined based on the user lifestyle, in addition to the other user information. For example, the metabolic loadings for a user with a heavily active lifestyle may differ from the metabolic loadings for a user with a sedentary lifestyle. In this fashion, the metabolic loadings may correspond with the user's particular characteristics.

In various embodiments, a computing device 708 (e.g., earphones 100 or computing device 200) stores or provides the metabolic loadings. Moreover, the metabolic loadings may be maintained or provided by server 706 or over communication medium 704. In one embodiment, a system administrator provides the metabolic loadings based on a survey, publicly available data, scientifically determined data, compiled user data, or any other source of data. In some instances, movement monitoring module 802 performs the above-described operations. In various embodiments, movement monitoring module 802 includes a metabolic loading module and a metabolic table module that determine the metabolic loading associated with the movement.

In one embodiment, a metabolic table is maintained based on the user information. The metabolic table may include metabolic loadings, which may be based on the user information. In some cases, the metabolic table is maintained based on standard user information, in place of or in addition to the user information. The standard user information may comprise, for example, the average fitness characteristics of all individuals being the same age as the user, the same height as the user, etc. In another embodiment, instead of maintaining the metabolic table based on standard information, if the user has not provided user information, maintaining the metabolic table is delayed until the user information is obtained.

Figure 8B:
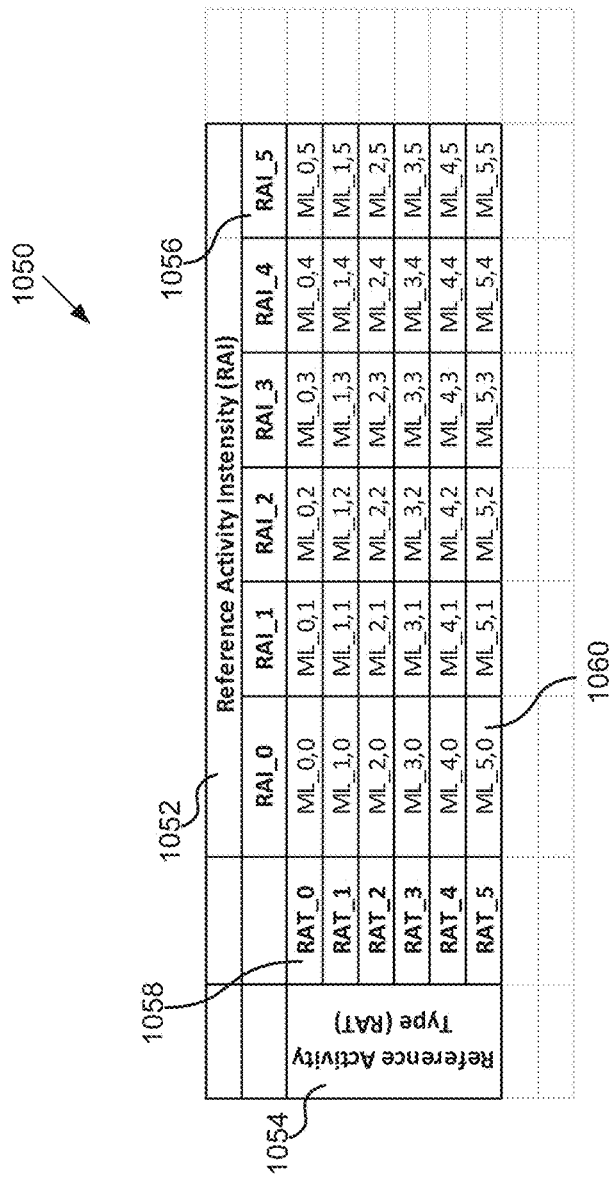
FIG. 8B is an example metabolic loading table

As illustrated in FIG. 8B, in one embodiment, the metabolic table is maintained as metabolic table 1050. Metabolic table 1050 may be stored in a storage of computing device 708 (e.g., memories 170, 175) or apparatus 702 (e.g., storage 202). Metabolic table 1050 may include information such as reference activity types (RATs) 1054, reference activity intensities (RAIs) 1052, and/or metabolic loadings (MLs) 1060.

In one embodiment, RATs 1054 are arranged as rows 1058 in metabolic table 1050. Thus, each of a set of rows 1058 corresponds to different RATs 1054, and each row 1058 is designated by a row index number. For example, the first RAT row 1058 may be indexed as RAT_0, the second as RAT_1, and so on for as many rows as metabolic table 1050 may include.

The reference activity types may include typical activities, such as running, walking, sleeping, swimming, bicycling, skiing, surfing, resting, working, and so on. The reference activity types may also include a catch-all category, for example, general exercise. The reference activity types may also include atypical activities, such as skydiving, SCUBA diving, and gymnastics. In one embodiment, the user defines a user-defined activity by programming computing device 708 or apparatus 702 (e.g., using application 210) with information about the user-defined activity, such as pattern of movement, frequency of pattern, and intensity of movement. The typical reference activities may be provided, for example, by metabolic table 1050.

In one embodiment, reference activity intensities 1052 are arranged as columns 1056 in metabolic table 1050, with each column 1056 corresponding to different RAIs 1052. Each column 1056 is designated by a different column index number. For example, the first RAI column 1056 is indexed as RAI_0, the second as RAI_1, and so on for as many columns 1056 as metabolic table 1050 may include.

The reference activity intensities include, in one embodiment, a numeric scale. By way of example, the reference activity intensities may include numbers ranging from one to ten (representing increasing activity intensity). The reference activities may also be represented as a range of letters, colors, and the like. The reference activity intensities may be associated with the vigorousness of an activity. For example, the reference activity intensities may represented by ranges of heart rates or breathing rates.

In one embodiment, metabolic table 1050 includes metabolic loadings 1060. Each metabolic loading 1060 corresponds to a reference activity type 1058 of the reference activity types 1054 and a reference activity intensity 1056 of the reference activity intensities 1052. Each metabolic loading 1060 corresponds to a unique combination of reference activity type 1054 and reference activity intensity 1052. For example, in the column and row arrangement discussed above, one of the reference activity types 1054 of a series of rows 1058 of reference activity types, and one of the reference activity intensities 1052 of a series of columns 1056 of reference activity intensities correspond to a particular metabolic loading 1060. In such an arrangement, each metabolic loading 1060 is identifiable by only one combination of reference activity type 1058 and reference activity intensity 1056.

This concept is illustrated in FIG. 8B. As shown, each metabolic loading 1060 is designated using a two-dimensional index, with the first index dimension corresponding to the row 1058 number and the second index dimension corresponding to the column 1056 number of the metabolic loading 1060. For example, in FIG. 8B, ML_2,3 has a first dimension index of 2 and a second dimension index of 3. ML_2,3 corresponds to the row 1058 for RAT_2 and the column 1056 for RAI_3. Any combination of RAT_M and RAI_N may identify a corresponding ML_M,N in metabolic table 1050, where M is any number corresponding to a row 1058 number in metabolic table 1050 and N is any number corresponding to a column 1056 number in metabolic table 1050. By way of example, the reference activity type RAT_3 may be "surfing," and the reference activity intensity RAI_3 may be "4." This combination in metabolic table 1050 corresponds to metabolic loading 1060 ML_3,3, which may, for example, represent 5.0 kcal/kg/hour (a typical value for surfing). In various embodiments, some of the above-described operations are performed by the movement monitoring module and some of the operations are performed by a metabolic table module (not shown).

Referring again to method 1000, in various embodiments, the movement is monitored by location tracking (e.g., Global Positioning Satellites (GPS) or by a location-tracking device connected to a network via communication medium 704). The general location of the user, as well as specific movements of the user's body, are monitored. For example, the movement of the user's leg in x, y, and z directions may be monitored using a motion sensor (e.g., by an accelerometer or gyroscope). In one embodiment, apparatus 702 receives an instruction regarding which body part is being monitored. For example, apparatus 702 may receive an instruction that the movement of a user's head, wrist, ankle, or torso is being monitored.

In various embodiments, the movement of the user is monitored and a pattern of the movement (pattern) is determined. The pattern may be detected by a motion sensor (e.g., accelerometer or gyroscope). The pattern may be a repetition of a motion or a similar motion monitored by the method 1000. For example, the pattern may be geometric shape (e.g., a circle, line, oval) of repeated movement that is monitored. In some cases, the repetition of the motion in the geometric shape is not repeated consistently over time, but is maintained for a substantial proportion of the repetitions of the movement. For instance, one pattern of elliptical motion in a repetitive pattern of ten circular motions may be monitored, and the pattern may be determined to be circular.

In further embodiments, the geometric shape of the pattern of movement is a three dimensional (3-D) shape. To illustrate, the pattern associated with the head of a person swimming freestyle may be monitored and analyzed as a geometric shape in three dimensions. The pattern may be described in a form can be recognized using method 1000. Such a form may include computer code that describes the spatial relationship of a set of points, along with changes in acceleration forces that are experienced along those points as, for example, a sensor travels through the pattern's trajectory.

In various embodiments, monitoring the pattern includes monitoring the frequency with which the pattern is repeated, i.e., the pattern frequency. The pattern frequency may be derived from a repetition period of the pattern, i.e., the pattern repetition period. The pattern repetition period may be the length of time elapsing from when a device or sensor passes through a certain point in a pattern and when the device or sensor returns to that point when the pattern is repeated. For example, the sensor may be at point x, y, z at time t_0. The device may then move along the trajectory of the pattern, eventually returning to point x, y, z at time t_1. The pattern repetition period would be the difference between t_1 and t_0 (e.g., measured in seconds). The pattern frequency may be the reciprocal of the pattern repetition period, and may have units of cycles per second. When the pattern repetition period is, for example, two seconds, the pattern frequency would be 0.5 cycles per second.

In some embodiments, various other inputs are used to determine the activity type and activity intensity. For example, monitoring the movement may include monitoring the velocity at which the user is moving (or the user velocity). The user velocity may have units of kilometers per hour. In one embodiment, the user's location information is monitored to determine the user velocity. This may be done by GPS, through communication medium 704, and so on. The user velocity may be distinguished from the speed of the pattern (or pattern speed). For example, the user may be swimming at a user velocity of 5 km/hour, but the pattern speed of the user's head may be 2 km/hour at a given point (e.g., as the head rotates between swimming strokes). The pattern speed may be monitored using, for example, an accelerometer or gyroscope.

In one embodiment, the user's altitude is monitored. This may be done, for example, using an altimeter, user location information, information entered by the user, etc. In another embodiment, the impact the user has with an object (e.g., the impact of the user's feet with ground) is monitored. This may be done using an accelerometer or gyroscope.

In some embodiments of method 1000, the ambient temperature is measured. A group of reference activity types may be associated with bands of ambient temperature. For example, when the ambient temperature is zero degrees Celsius, activities such as skiing, sledding, and ice climbing are appropriate selections for reference activity types, whereas surfing, swimming, and beach volleyball may be inappropriate. In further embodiments, the humidity may be measured (e.g., by a hygrometer). In yet further embodiments, the pattern duration—the length of time for which particular movement pattern is sustained—is measured.

Monitoring the movement, in one embodiment, is accomplished using sensors configured to be attached to the user's body. Such sensors may include a gyroscope or accelerometer to detect movement, and a heart-rate sensor, each of which may be embedded in earphones that a user can wear, such as earphones 100. Additionally, various modules and sensors that may be used to perform the above-described operations may be embedded in electronic components of earphones 100 such as, for example, processor 165 and memory 175. In various embodiments, the above-described operations are performed by the movement monitoring module.

Method 1000, in one embodiment, involves determining the user activity type from the set of reference activity types. Once detected, the pattern may be used to determine the user activity type from the set of reference activity types. Each reference activity type is associated with a reference activity type pattern. The user activity type may be determined to be the reference activity type that has a reference activity type pattern that matches the pattern detected by method 1000.

In some cases, the pattern that matches the reference activity type pattern will not be an exact match, but will be substantially similar. In other cases, the patterns will not even be substantially similar, but it may be determined that the patterns match because they are the most similar of any patterns available. For example, the reference activity type may be determined such that the difference between the pattern of movement corresponding to the reference activity type and the pattern of movement is less than a predetermined threshold. In one embodiment, the pattern is looked up (for a match) in a reference activity type library. The reference activity type library may be included in metabolic table 1050. For example, the reference type library may include rows in a table such as the RAT rows 1058.

In further embodiments, method 1000 involves using the pattern frequency to determine the user activity type from the set of reference activity types. Several reference activity types may be associated with similar patterns (e.g., because the head moves in a similar pattern when running versus walking). In such cases, the pattern frequency may be used to determine the user activity type (e.g., because the pattern frequency for running is higher than the pattern frequency for walking).

Method 1000, in some instances, involves using additional information to determine the user activity type. For example, the pattern for walking may be similar to the pattern for running. The reference activity type of running may be associated with higher user velocities and the reference activity type of walking with lower user velocities. In this way, the velocity measured may be used to distinguish between two reference activity types having similar patterns.

In other embodiments, method 1000 involves monitoring the impact the user has with the ground and determining that, because the impact is larger, the activity type is running rather than walking, for example. If there is no impact, the user activity type may be determined to be cycling (or other activity type where there is no impact). In some cases, the humidity is measured to determine whether the user activity type is a water sport (i.e., whether the activity is being performed in the water). The reference activity types may be narrowed to those that are performed in the water, from which narrowed set of reference activity types the user activity type may be determined. In other cases, the temperature measured is used to determine the user activity type.

Method 1000 may entail instructing the user to confirm the user activity type. In one embodiment, a user interface is provided (e.g., using application 210) such that the user can confirm whether a displayed user activity type is correct or select the user activity type from a group of reference activity types.

In further embodiments, a statistical likelihood of choices for user activity type is determined. The possible user activity types are then provided to the user in such a sequence that the most likely user activity type is listed first (and then in descending order of likelihood). For example, it may be determined, based on the pattern, the pattern frequency, the temperature, and so on, that there is an 80% chance the user activity type is running, a 15% chance the user activity type is walking, and a 5% chance the user activity type is dancing. Via a user interface (e.g., using app 210), a list of these possible user activity types may be provided such that the user may select the user activity type the user is performing. In various embodiments, some of the above-described operations are performed by a metabolic loading module.

Figure 8C:
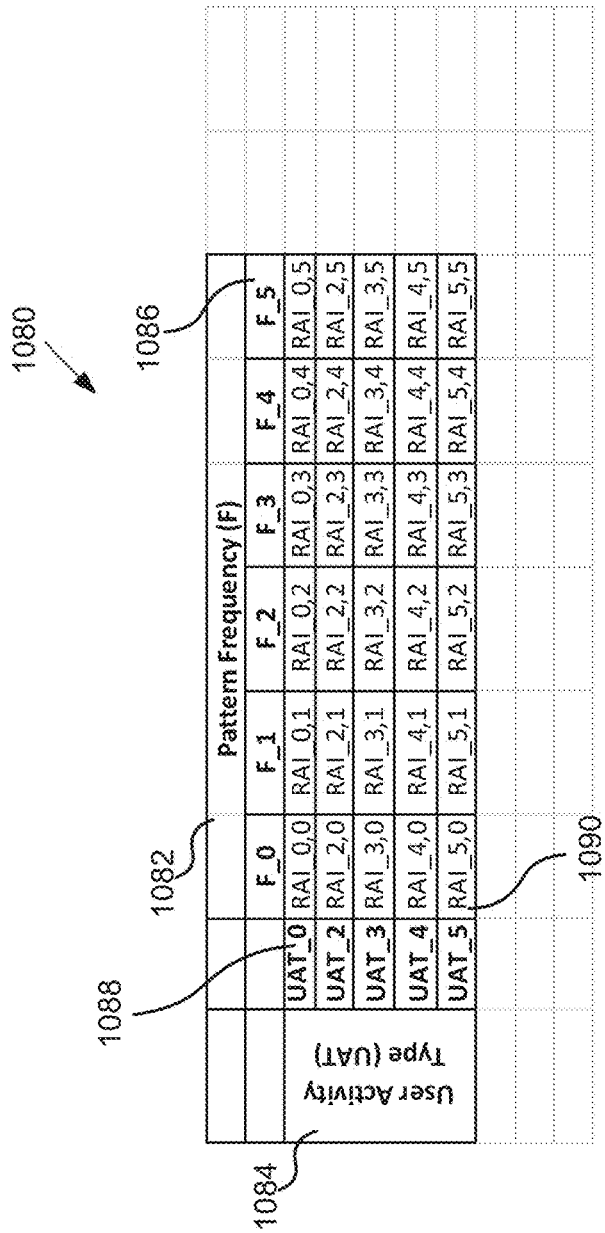
FIG. 8C is an example activity intensity library.

Method 1000, in some embodiments, also includes determining the user activity intensity from a set of reference activity intensities. The user activity intensity may be determined in a variety of ways. For example, the repetition period (or pattern frequency) and user activity type (UAT) may be associated with a reference activity intensity library to determine the user activity intensity that corresponds to a reference activity intensity. FIG. 8C illustrates one embodiment whereby this aspect of method 1000 is accomplished, including reference activity intensity library 1080. Reference activity intensity library 1080 is organized by rows 1088 of reference activity types 1084 and columns 1086 of pattern frequencies 1082. In FIG. 8C, reference activity library 1080 is implemented in a table. Reference activity library 1080 may, however, be implemented other ways.

In one embodiment, it is determined that, for user activity type 1084 UAT_0 performed at pattern frequency 1082 F_0, the reference activity intensity 1090 is RAI_0,0. UAT 1084 may, for example, correspond to the reference activity type for running, and a pattern frequency 1082 of 0.5 cycles per second for the user activity type may be determined. In addition, library 1080 may determine (e.g., at operation 1002) that the UAT 1084 of running at a pattern frequency 1082 of 0.5 cycles per second corresponds to an RAI 1090 of five on a scale of ten. In another embodiment, the reference activity intensity is independent of the activity type. For example, the repetition period may be five seconds, and this may correspond to an intensity level of two on a scale of ten regardless of the user activity type.

Reference activity intensity library 1080, in one embodiment, is included in metabolic table 1050. In some cases, the measured repetition period (or pattern frequency) does not correspond exactly to a repetition period for a reference activity intensity in metabolic table 1050. In such cases, the correspondence may be a best-match fit, or may be a fit within a tolerance defined by the user or by a system administrator, for example.

In various embodiments, method 1000 involves supplementing the measurement of pattern frequency to help determine the user activity intensity from the reference activity intensities. For example, if the user activity type is skiing, it may be difficult to determine the user activity intensity because the pattern frequency may be erratic or otherwise immeasurable. In such an example, the user velocity, the user's heart rate, and other indicators (e.g., breathing rate) may be monitored to determine how hard the user is working during the activity. For example, higher heart rate may indicate higher user activity intensity. In a further embodiment, the reference activity intensity is associated with a pattern speed (i.e., the speed or velocity at which a sensor is progressing through the pattern). A higher pattern speed may correspond to a higher user activity intensity.

Method 1000, in one embodiment, determines the user activity type and the user activity intensity using sensors attached to the user's body. Such sensors may include, for example, a gyroscope or accelerometer to detect movement, and a heart-rate sensor, each of which may be embedded in earphones that the user can wear on the user's head, such as earphones 100. Additionally, various sensors and modules that may be used to perform above-described operations of method 1000 may be embedded in earphones 100. In various embodiments, the above-described operations are performed by the movement monitoring module.

In one embodiment, method 1000 includes creating and updating a metabolic activity scored based on the user movement and user information. Method 1000 may also include determining a metabolic loading associated with the user and the movement. In one embodiment, a duration of the activity type at a particular activity intensity (e.g., in seconds, minutes, or hours) is determined. The metabolic activity score may be created and updated by, for example, multiplying the metabolic loading by the duration of the user activity type at a particular user activity intensity. If the user activity intensity changes, the new metabolic loading (associated with the new user activity intensity) may be multiplied by the duration of the user activity type at the new user activity intensity. In one embodiment, the activity score is represented as a numerical value. By way of example, the metabolic activity score may be updated by continually supplementing the metabolic activity score as new activities are undertaken by the user. In this way, the metabolic activity score continually increases as the user participates in more and more activities.

Referring again to FIG. 8A, At operation 1004, a fatigue level is detected. In one embodiment, the fatigue level is the fatigue level of the user. In one embodiment, the fatigue level is a function of recovery. In various embodiments, the fatigue level is described in terms of recovery. The fatigue level may be detected in various ways. In one example, the fatigue level is detected by calculating a heart rate variability (HRV) of the user using optical heartrate sensor 122 (discussed above in reference to FIG. 2B). Further, possible representations of the fatigue level are described above (e.g., numerical, descriptive, etc.). When the HRV is more consistent (i.e., steady, consistent amount of time between heartbeats), for example, the fatigue level may be higher. In other words, with a higher fatigue level, the body is typically less fresh and less well-rested. When HRV is more sporadic (i.e., amount of time between heartbeats varies largely), the fatigue level may be lower. In various embodiments, the fatigue level is described in terms of an HRV score.

HRV may be measured in a number of ways (e.g., as discussed above in reference to FIGS. 2B and 3A-3C). Measuring HRV, in one embodiment, involves optical heartrate sensor 122 measuring changes in blood flow. Light reflected back through the skin of the user's ear may be obtained with a receiver (e.g., a photodiode) and used to determine changes in the user's blood flow, thereby permitting calculation of the user's heart rate using algorithms known in the art. Using the data collected by sensor 122, processor 165 may calculate the HRV based on a time domain methods, frequency domain methods, and other methods known in the art that calculate HRV based on data such as the mean heart rate, the change in pulse rate over a time interval, and other data used in the art to estimate HRV. In other embodiments, HRV may be measured using electrocardiography (ECG) or photoplethysmography (PPG) sensors mounted on other parts of the user's body, such as, for example, sensors mounted on the wrist, finger, ankle, leg, arm, or chest.

In one embodiment, at operation 1004, the fatigue level is detected based solely on the determined HRV. The fatigue level, however, may be based on other measurements (e.g., measurements monitored by method 1000). For example, the fatigue level may be based on the amount of sleep that is measured for the previous night, the user activity duration, the user activity type, and the user activity intensity determined for a previous time period (e.g., exercise activity level in the last twenty-four hours).

By way of example, other measurements on which the fatigue level may be based include stress-related activities, such as work and driving in traffic, which may generally cause the user to become fatigued. In some cases, the fatigue level is detected by comparing the HRV measured to a reference HRV. The reference HRV may be based on information gathered from a large number of people from the general public. In another embodiment, the reference HRV is based on past measurements of the user's HRV.

At operation 1004, in one embodiment, the fatigue level is detected once every twenty-four hours. This provides information about the user's fatigue level each day so that the user's activity levels may be directed according to the fatigue level. In various embodiments, the fatigue level is detected more or less often. Using the fatigue level, the user may determine (a) whether or not an activity is necessary (or desirable), (b) the appropriate user activity intensity, and (c) the appropriate user activity duration. For example, in deciding whether to go on a run, or how long to run, the user may want to use operation 1004 to assess the user's current fatigue level. Then, the user may, for example, run for a shorter time if the user is more fatigued, or for a longer time if the user is less fatigued. In some cases, it may be beneficial to detect the fatigue level in the morning when the user wakes up. This may provide the user a reference for how the day's activities should proceed.

Referring again to FIG. 8A, at operation 1006 a dynamic load schedule is created and updated by modifying the initial load schedule based on the user's fatigue level. In one embodiment, the initial load schedule is modified based on the fatigue level to prevent the user from becoming over-fatigued or under-fatigued. If the user becomes over-fatigued, the user may be too tired and may not be able to achieve peak performance. If the user is under-fatigued, the user may be to recovered and may not be sharp enough to achieve peak performance. In other words, by avoiding under and over fatigue, the dynamic load schedule positions the user in an optimal performance zone. By creating the dynamic load schedule, method 1000 provides a load schedule that adapts to the user's actual fatigue level. In one embodiment, the dynamic load schedule is, in form, substantially similar to the initial load schedule. For example, the dynamic load schedule may include a recommended daily activity level—e.g., in the form of metabolic activity score. In addition, the dynamic load schedule may include a recommended fatigue level.

In one embodiment, through continual updates based on the user's fatigue level, the dynamic load schedule prepares a user for an event to take place on a specified date. The dynamic load schedule, in one instance, provides a recommendation for activity level to the user, for example, in the form of a metabolic activity score. By following the recommendation for activity level (or recommendation for fatigue level), the user may be able to build up the endurance and strength required for the event taking place on the specified date.

In addition, being tuned to the user's fatigue level, the dynamic load schedule, in one embodiment, places the user in position for peak performance (or an optimal performance zone) and recovery on the date of the specified event. In other words, the user may be positioned in a recovery state—or at a fatigue level—in which the user is neither over-fatigued or under-fatigued. Peak performance (or optimal performance zone), may correspond to, for example, a fatigue level of between 40 and 60. In such an example, the dynamic load schedule would position the user at a fatigue level of between 40 and 60 on the day of the event. For some users, however, the peak performance zone may be different, and method 1000 may determine the user's specific peak performance and recovery position by tracking the user's performance over time.

In one embodiment, the initial load schedule is provided by calculating the number of days it would take for a typical user to prepare for a specified event at a future date. In such an embodiment, the user may have characteristics different from the assumed user characteristics used to create the initial load schedule. As a result, the initial load schedule may not be tailored to the user. The dynamic load schedule, being based on the user's fatigue levels, may be tailored to the user's actual, physical response from undergoing activity, including resting from the activity.

Updating the dynamic load schedule, in one embodiment, occurs in response to detecting the fatigue level. This may be done, for example, in real time following the detection of the fatigue level at operation 1004. In one instance, the user may not desire for the dynamic load schedule to be updated in response to detecting the fatigue level. For example, if the user suspects that the fatigue level detected is inaccurate—e.g., due to user error—the user may desire to keep the non-updated dynamic load schedule because the updated version would be inaccurate. In one embodiment, the dynamic load schedule is stored upon creation (or upon being updated), such that, if the dynamic load schedule is updated contrary to the user's desire, the dynamic load schedule may be restored to a past state. The dynamic load schedule, in one embodiment, is updated at least once per day following detection of the fatigue level.

In further embodiments, the user's movement may be monitored using the movement monitoring module (which may include a motion sensor) in combination with the fatigue level module (which may include a heartrate sensor) to determine the user's compliance with the dynamic load schedule. For example, the user's activity (e.g., running) and activity level (e.g., lower, moderate, high) for the day may be compared with a recommended daily activity and activity level provided by the dynamic load schedule.

Figure 9:
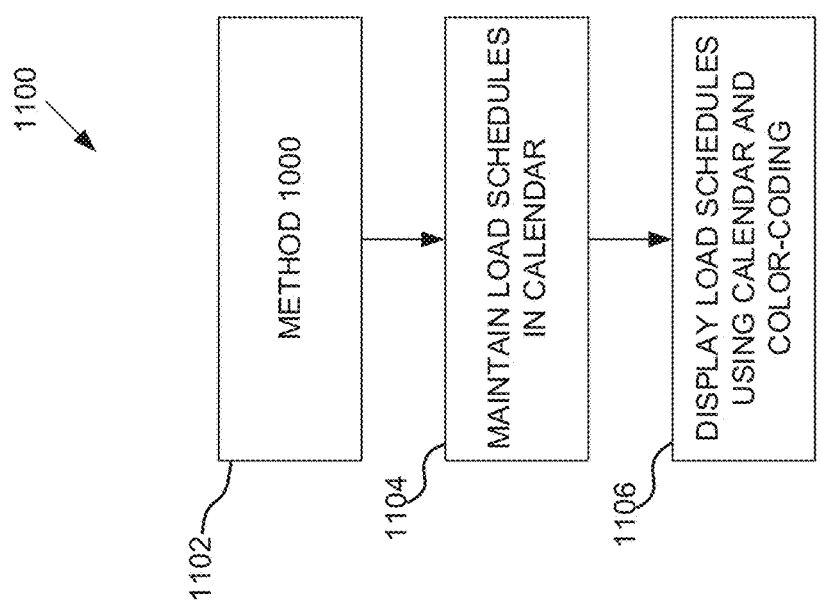
FIG. 9 is an operational flow diagram illustrating another example method for providing a user a training load schedule.

FIG. 9 is an operational flow diagram illustrating an example method 1100 for providing a training load schedule for peak performance positioning. In one embodiment, earphones 100 and computing device 200 may perform various operations of method 1100. Method 1100, in various embodiments, includes the operations of method 1000.

At operation 1104, the initial load schedule and dynamic load schedules are maintained in a calendar. For example, the initial load schedule and the dynamic load schedule may be maintained as recommended activity or fatigue levels for each day represented on a week or month calendar. Other variations would be appreciated by one having ordinary skill in the art. The initial load schedule and the dynamic load schedule, in one embodiment, are maintained in the calendar with various graphical presentations. For example, the graphical presentation may include a line graph spanning multiple days that shows the recommended load schedule (initial or dynamic). In one instance, the dynamic load schedule may be displayed overlaying the initial load schedule. This example display provides a quick comparison between the initial load schedule and the dynamic load schedule.

Referring again to FIG. 9, at operation 1106 the initial load schedule and the dynamic load schedule are displayed using the calendar and at least one of a color-coding representation and a numerical representation. For example, the initial load schedule and the dynamic load schedule may be represented as a numerical value on the calendar (e.g., dynamic load schedule for Oct. 12, 2014, may be 2,000).

Moreover, the initial and dynamic load schedules may be represented using a series of colors to indicate the recommended load. For example, red may indicate a high recommended load (i.e., very active day), yellow may indicate a moderate load (i.e., normally active day), and green may indicate a light load (i.e., restful day). In another example, the color might indicate whether the user is on pace to be prepared for the specified event. This provides for at-a-glance, understandable information that the user can rely on to direct the user's activities. In a further embodiment, the load schedules are presented using a combination of numerical, color-coded, and graphical representations.

Figure 10:
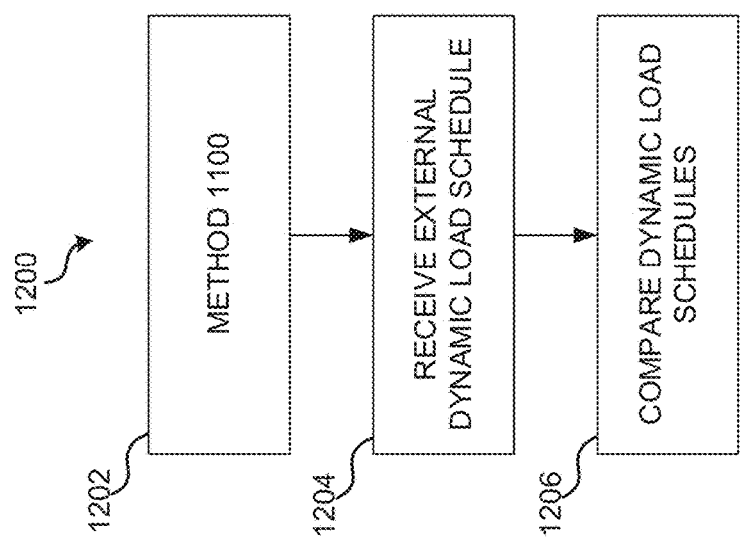
FIG. 10 is an operational flow diagram illustrating another example method for providing a user a training load schedule.

FIG. 10 is an operational flow diagram illustrating an example method 1200 for providing a training load schedule for peak performance positioning in accordance with an embodiment of the present disclosure. In one embodiment, earphones 100 and computing device 200 may perform various operations of method 1100. Method 1200, in various embodiments, includes the operations of method 1100.

At operation 1204, an external dynamic load schedule is received. The external dynamic load schedule may be received in a number of ways (e.g., via communication medium 704). The external dynamic load schedule may be created and updated in a manner similar to the creating and updating of the dynamic load schedule (e.g., at operation 1006). The external dynamic load schedule may be from a second user, who is any user other than the user that received the external dynamic load schedule. For example, the second user may be a friend or associate of the first user.

In one embodiment, the external dynamic load schedule is a past dynamic load schedule of the user that is associated with a past event. For example, the external dynamic load schedule may be the user's dynamic load schedule for a 2013 marathon event. In this manner, method 1200 provides the user the ability to train against the user's past training regimens. In various embodiments, operation 1204 is performed by dynamic load schedule module 806.

At operation 1206, the dynamic load schedule is compared to the external dynamic load schedule. Operation 1206, in one embodiment, entails displaying a graphical, numerical, or color-coded representation of the dynamic load schedule. The representation of the dynamic load schedule may be overlaid with a similar representation of the external dynamic load schedule. As would be appreciated by one having skill in the art, the load schedules may be compared in a number of ways. In another embodiment, the dynamic load schedule is compared to multiple external dynamic load schedules associated with other users. In a further embodiment, the dynamic load schedule is compared to multiple past dynamic load schedules of the user that are associated with multiple past events. This provides a metric whereby the user can ghost train against the user's own past performance training in a set of past events that may be similar to the upcoming event.

Accordingly, operation 1206 permits a user to compare the user's dynamic load schedule, which is based on the user's fatigue level and a specified future event, to the external dynamic load schedule of other users, which may also be based on the other users' fatigue levels and specified future events. In embodiments where the user specified event and the external user(s) specified event are the same, the user is provided with a relative metric for the user's preparation for the specified event. This may allow the user to compete against the other users as the user and the others train and for the upcoming event. In various embodiments, operation 1206 is performed using dynamic load schedule module 806.

In one embodiment, operations of method 1000, method 1100, and method 1200 are performed using sensors configured to be attached to the body (e.g., the user's body). Such sensors may include, for example, a gyroscope or accelerometer to detect movement (e.g., motion sensor 121), and a heart-rate sensor (e.g., optical heartrate sensor 122), each of which may be embedded, for example, in earphones 100. Such sensors may be used to perform operations such as monitoring the user's movement, and detecting the user's fatigue level. Additionally, such sensors may assist in providing the initial load schedule and creating and updating the dynamic load schedule, and any other operation disclosed herein. For example, in one particular embodiment computing device 200 may execute application 210 to create and update the load schedules based on readings from the biometric sensors of earphones 100.

FIGS. 11-14 illustrate a particular implementation of a GUI for activity tracking application 210 comprising displays associated with each of display modules 211-214. In various embodiments, the GUI of activity tracking application 210 may be used to provide to a user a training load schedule for peak performance.

Figure 11:
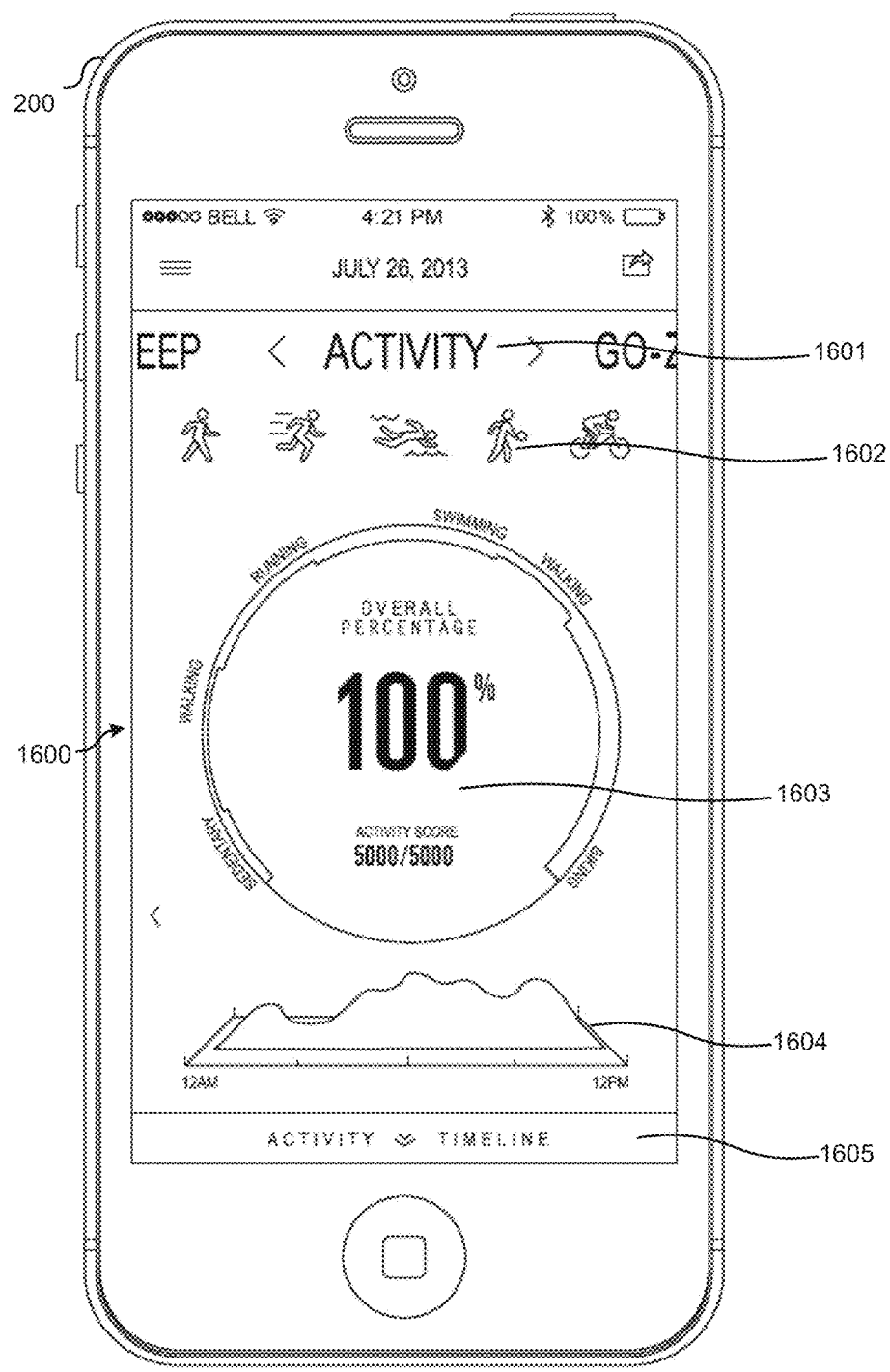
FIG. 11 illustrates an activity display that may be associated with an activity display module of the activity monitoring application of FIG. 4B.

FIG. 11 illustrates an activity display 1600 that may be associated with an activity display module 211. In various embodiments, activity display 1600 may visually present to a user a record of the user's activity. As illustrated, activity display 1600 may comprise a display navigation area 1601, activity icons 1602, activity goal section 1603, live activity chart 1604, and activity timeline 1605. As illustrated in this particular embodiment, display navigation area 1601 allows a user to navigate between the various displays associated with modules 211-214 by selecting "right" and "left" arrows depicted at the top of the display on either side of the display screen title. An identification of the selected display may be displayed at the center of the navigation area 1601. Other selectable displays may displayed on the left and right sides of navigation area 1601. For example, in this embodiment the activity display 1600 includes the identification "ACTIVITY" at the center of the navigation area. If the user wishes to navigate to a sleep display in this embodiment, the user may select the left arrow. In implementations where device 200 includes a touch screen display, navigation between the displays may be accomplished via finger swiping gestures. For example, in one embodiment a user may swipe the screen right or left to navigate to a different display screen. In another embodiment, a user may press the left or right arrows to navigate between the various display screens.

In various embodiments, activity icons 1602 may be displayed on activity display 1600 based on the user's predicted or self-reported activity. For example, in this particular embodiment activity icons 1602 are displayed for the activities of walking, running, swimming, sport, and biking, indicating that the user has performed these five activities. In one particular embodiment, one or more modules of application 210 may estimate the activity being performed (e.g., sleeping, walking, running, or swimming) by comparing the data collected by a biometric earphone's sensors to pre-loaded or learned activity profiles. For example, accelerometer data, gyroscope data, heartrate data, or some combination thereof may be compared to preloaded activity profiles of what the data should look like for a generic user that is running, walking, or swimming. In implementations of this embodiment, the preloaded activity profiles for each particular activity (e.g., sleeping, running, walking, or swimming) may be adjusted over time based on a history of the user's activity, thereby improving the activity predictive capability of the system. In additional implementations, activity display 1600 allows a user to manually select the activity being performed (e.g., via touch gestures), thereby enabling the system to accurately adjust an activity profile associated with the user-selected activity. In this way, the system's activity estimating capabilities will improve over time as the system learns how particular activity profiles match an individual user. Particular methods of implementing this activity estimation and activity profile learning capability are described in U.S. patent application Ser. No. 14/568,835, filed Dec. 12, 2014, titled "System and Method for Creating a Dynamic Activity Profile", and which is incorporated herein by reference in its entirety.

In various embodiments, an activity goal section 1603 may display various activity metrics such as a percentage activity goal providing an overview of the status of an activity goal for a timeframe (e.g., day or week), an activity score or other smart activity score associated with the goal, and activities for the measured timeframe (e.g., day or week). For example, the display may provide a user with a current activity score for the day versus a target activity score for the day. Particular methods of calculating activity scores are described in U.S. patent application Ser. No. 14/137,734, filed Dec. 20, 2013, titled "System and Method for Providing a Smart Activity Score", and which is incorporated herein by reference in its entirety.

In various embodiments, the percentage activity goal may be selected by the user (e.g., by a touch tap) to display to the user an amount of a particular activity (e.g., walking or running) needed to complete the activity goal (e.g., reach 100%). In additional embodiments, activities for the timeframe may be individually selected to display metrics of the selected activity such as points, calories, duration, or some combination thereof. For example, in this particular embodiment activity goal section 1603 displays that 100% of the activity goal for the day has been accomplished. Further, activity goal section 1603 displays that activities of walking, running, biking, and no activity (sedentary) were performed during the day. This is also displayed as a numerical activity score 5000/5000. In this embodiment, a breakdown of metrics for each activity (e.g., activity points, calories, and duration) for the day may be displayed by selecting the activity.

A live activity chart 1604 may also display an activity trend of the aforementioned metrics (or other metrics) as a dynamic graph at the bottom of the display. For example, the graph may be used to show when user has been most active during the day (e.g., burning the most calories or otherwise engaged in an activity).

An activity timeline 1605 may be displayed as a collapsed bar at the bottom of display 1600. In various embodiments, when a user selects activity timeline 1605, it may display a more detailed breakdown of daily activity, including, for example, an activity performed at a particular time with associated metrics, total active time for the measuring period, total inactive time for the measuring period, total calories burned for the measuring period, total distance traversed for the measuring period, and other metrics.

Figure 12:
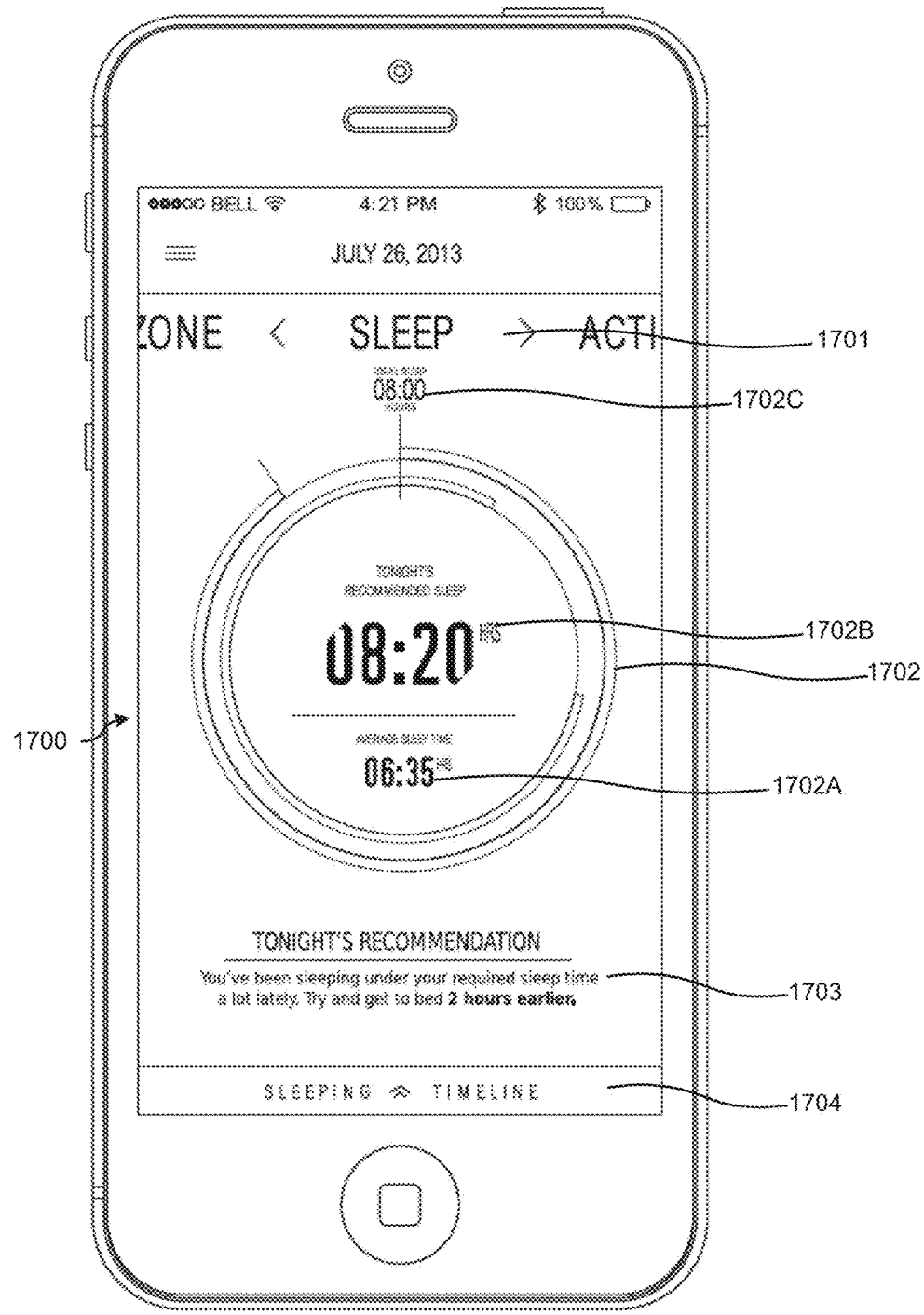
FIG. 12 illustrates a sleep display that may be associated with a sleep display module of the activity monitoring application of FIG. 4B.

FIG. 12 illustrates a sleep display 1700 that may be associated with a sleep display module 1712. In various embodiments, sleep display 1700 may visually present to a user a record of the user's sleep history and sleep recommendations for the day. It is worth noting that in various embodiments one or more modules of the activity tracking application 1710 may automatically determine or estimate when a user is sleeping (and awake) based on an a preloaded or learned activity profile for sleep, in accordance with the activity profiles described above. Alternatively, the user may interact with the sleep display 1700 or other display to indicate that the current activity is sleep, enabling the system to better learn that individualized activity profile associated with sleep. The modules may also use data collected from the earphones, including fatigue level and activity score trends, to calculate a recommended amount of sleep. Systems and methods for implementing this functionality are described in greater detail in U.S. patent application Ser. No. 14/568,835, filed Dec. 12, 2014, and titled "System and Method for Creating a Dynamic Activity Profile", and U.S. patent application Ser. No. 14/137,942, filed Dec. 20, 2013, titled "System and Method for Providing an Interpreted Recovery Score," both of which are incorporated herein by reference in their entirety.

As illustrated, sleep display 1700 may comprise a display navigation area 1701, a center sleep display area 1702, a textual sleep recommendation 1703, and a sleeping detail or timeline 1704. Display navigation area 1701 allows a user to navigate between the various displays associated with modules 211-214 as described above. In this embodiment the sleep display 1700 includes the identification "SLEEP" at the center of the navigation area 1701.

Center sleep display area 1702 may display sleep metrics such as the user's recent average level of sleep or sleep trend 1702A, a recommended amount of sleep for the night 1702B, and an ideal average sleep amount 1702C. In various embodiments, these sleep metrics may be displayed in units of time (e.g., hours and minutes) or other suitable units. Accordingly, a user may compare a recommended sleep level for the user (e.g., metric 1702B) against the user's historical sleep level (e.g., metric 1702A). In one embodiment, the sleep metrics 1702A-1702C may be displayed as a pie chart showing the recommended and historical sleep times in different colors. In another embodiment, sleep metrics 1702A-1702C may be displayed as a curvilinear graph showing the recommended and historical sleep times as different colored, concentric lines. This particular embodiment is illustrated in example sleep display 1700, which illustrates an inner concentric line for recommended sleep metric 1702B and an outer concentric line for average sleep metric 1702A. In this example, the lines are concentric about a numerical display of the sleep metrics.

In various embodiments, a textual sleep recommendation 1703 may be displayed at the bottom or other location of display 1700 based on the user's recent sleep history. A sleeping detail or timeline 1704 may also be displayed as a collapsed bar at the bottom of sleep display 1700. In various embodiments, when a user selects sleeping detail 1704, it may display a more detailed breakdown of daily sleep metrics, including, for example, total time slept, bedtime, and wake time. In particular implementations of these embodiments, the user may edit the calculated bedtime and wake time. In additional embodiments, the selected sleeping detail 1704 may graphically display a timeline of the user's movements during the sleep hours, thereby providing an indication of how restless or restful the user's sleep is during different times, as well as the user's sleep cycles. For the example, the user's movements may be displayed as a histogram plot charting the frequency and/or intensity of movement during different sleep times.

Figure 13:
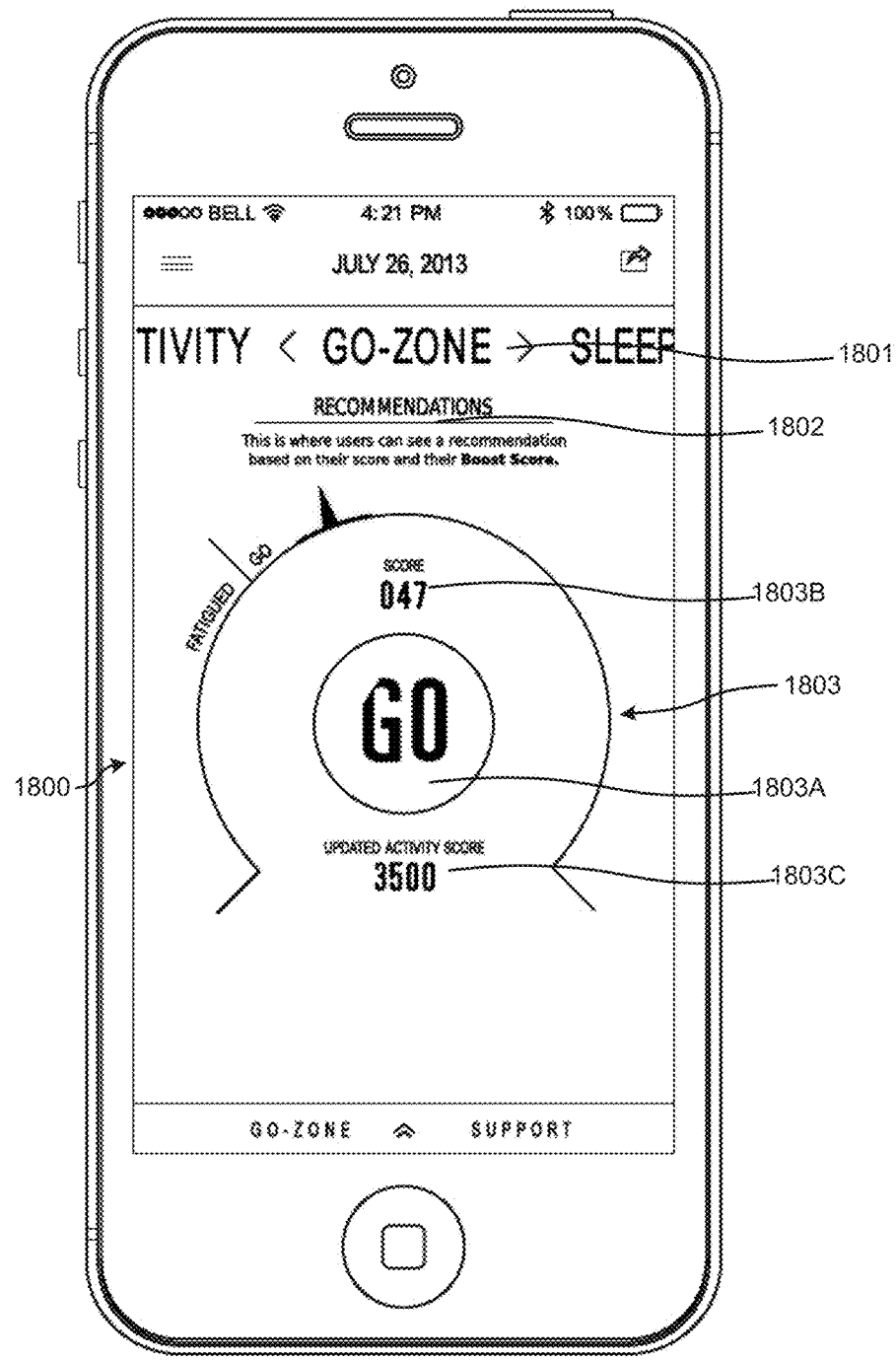
FIG. 13 illustrates an activity recommendation and fatigue level display that may be associated with an activity recommendation and fatigue level display module of the activity monitoring application of FIG. 4B.

FIG. 13 illustrates an activity recommendation and fatigue level display 1800 that may be associated with an activity recommendation and fatigue level display module 213. In various embodiments, display 1800 may visually present to a user the user's current fatigue level and a recommendation of whether or not engage in activity. It is worth noting that one or more modules of activity tracking application 210 may track fatigue level based on data received from the earphones 100, and make an activity level recommendation. For example, HRV data tracked at regular intervals may be compared with other biometric or biological data to determine how fatigued the user is. Additionally, the HRV data may be compared to pre-loaded or learned fatigue level profiles, as well as a user's specified activity goals. Particular systems and methods for implementing this functionality are also described in greater detail in U.S. patent application Ser. No. 14/140,414, filed Dec. 24, 2013, titled "System and Method for Providing an Intelligent Goal Recommendation for Activity Level", and which is incorporated herein by reference in its entirety.

As illustrated, display 1800 may comprise a display navigation area 1801 (as described above), a textual activity recommendation 1802, and a center fatigue and activity recommendation display 1803. Textual activity recommendation 1002 may, for example, display a recommendation as to whether a user is too fatigued for activity, and thus must rest, or if the user should be active. Center display 1803 may display an indication to a user to be active (or rest) 1803A (e.g., "go"), an overall score 1803B indicating the body's overall readiness for activity, and an activity goal score 1803C indicating an activity goal for the day or other period. In various embodiments, indication 1803A may be displayed as a result of a binary decision—for example, telling the user to be active, or "go"—or on a scaled indicator—for example, a circular dial display showing that a user should be more or less active depending on where a virtual needle is pointing on the dial.

In various embodiments, display 1800 may be generated by measuring the user's HRV at the beginning of the day (e.g., within 30 minutes of waking up.) For example, the user's HRV may be automatically measured using the optical heartrate sensor 122 after the user wears the earphones in a position that generates a good signal as described in method 400. In embodiments, when the user's HRV is being measured, computing device 200 may display any one of the following: an instruction to remain relaxed while the variability in the user's heart signal (i.e., HRV) is being measured, an amount of time remaining until the HRV has been sufficiently measured, and an indication that the user's HRV is detected. After the user's HRV is measured by earphones 100 for a predetermined amount of time (e.g., two minutes), one or more processing modules of computing device 200 may determine the user's fatigue level for the day and a recommended amount of activity for the day. Activity recommendation and fatigue level display 1800 is generated based on this determination.

In further embodiments, the user's HRV may be automatically measured at predetermined intervals throughout the day using optical heartrate sensor 122. In such embodiments, activity recommendation and fatigue level display 1800 may be updated based on the updated HRV received throughout the day. In this manner, the activity recommendations presented to the user may be adjusted throughout the day.

Figure 14:
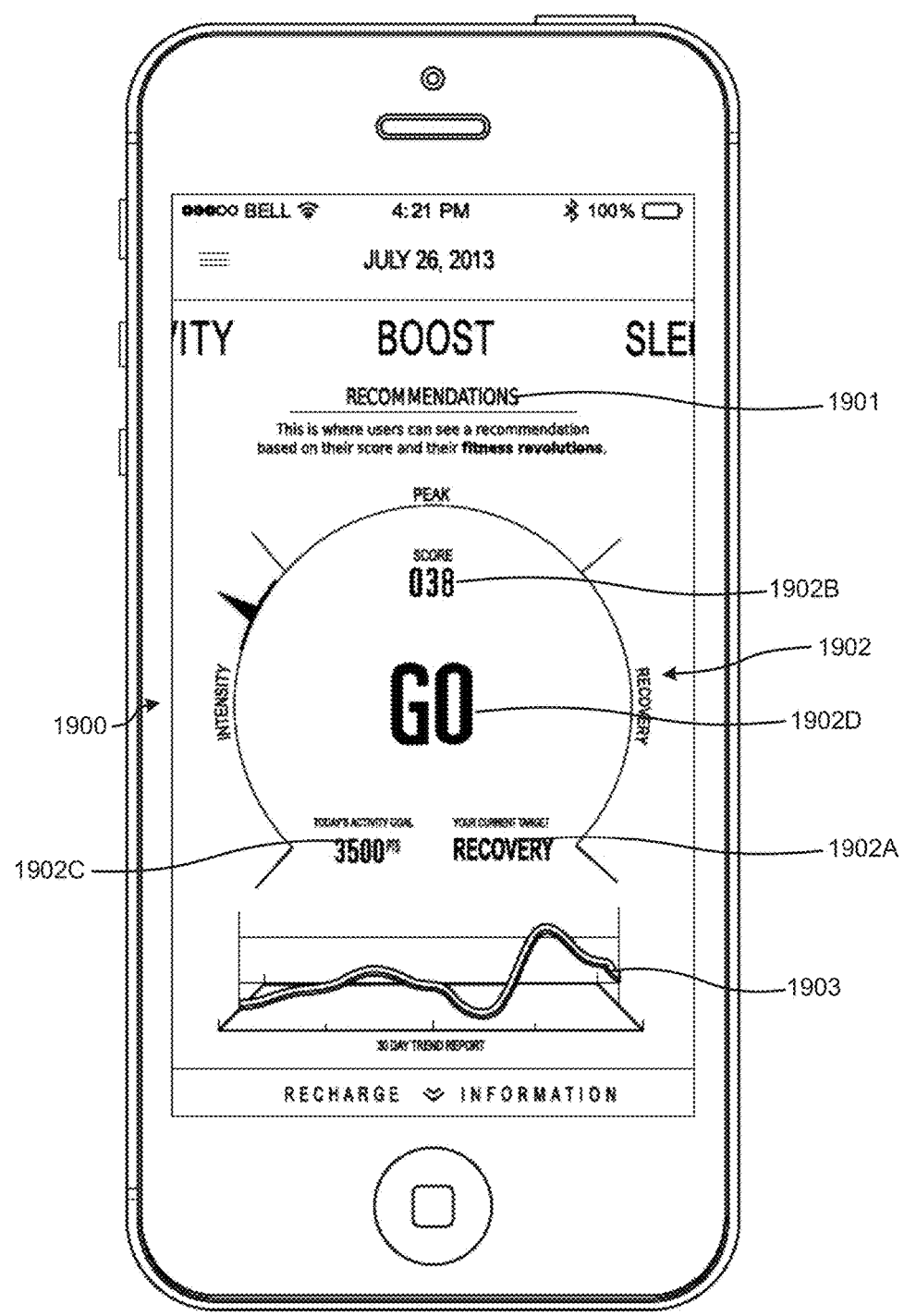
FIG. 14 illustrates a biological data and intensity recommendation display that may be associated with a biological data and intensity recommendation display module of the activity monitoring application of FIG. 4B.

FIG. 14 illustrates a biological data and intensity recommendation display 1900 that may be associated with a biological data and intensity recommendation display module 214. In various embodiments, display 1900 may guide a user of the activity monitoring system through various fitness cycles of high-intensity activity followed by lower-intensity recovery based on the user's body fatigue and recovery level, thereby boosting the user's level of fitness and capacity on each cycle.

As illustrated, display 1900 may include a textual recommendation 1901, a center display 1902, and a historical plot 1903 indicating the user's transition between various fitness cycles. In various embodiments, textual recommendation 1901 may display a current recommended level of activity or training intensity based on current fatigue levels, current activity levels, user goals, pre-loaded profiles, activity scores, smart activity scores, historical trends, and other bio-metrics of interest. Center display 1902 may display a fitness cycle target 1902A (e.g., intensity, peak, fatigue, or recovery), an overall score 1902B indicating the body's overall readiness for activity, an activity goal score 1902C indicating an activity goal for the day or other period, and an indication to a user to be active (or rest) 1902D (e.g., "go"). The data of center display 1902 may be displayed, for example, on a virtual dial, as text, or some combination thereof. In one particular embodiment implementing a dial display, recommended transitions between various fitness cycles (e.g., intensity and recovery) may be indicated by the dial transitioning between predetermined markers.

In various embodiments, display 1900 may display a historical plot 1903 that indicates the user's historical and current transitions between various fitness cycles over a predetermined period of time (e.g., 30 days). The fitness cycles, may include, for example, a fatigue cycle, a performance cycle, and a recovery cycle. Each of these cycles may be associated with a predetermined score range (e.g., overall score 1902B). For example, in one particular implementation a fatigue cycle may be associated with an overall score range of 0 to 33, a performance cycle may be associated with an overall score range of 34 to 66, and a recovery cycle may be associated with an overall score range of 67 to 100. The transitions between the fitness cycles may be demarcated by horizontal lines intersecting the historical plot 1903 at the overall score range boundaries. For example, the illustrated historical plot 1903 includes two horizontal lines intersecting the historical plot. In this example, measurements below the lowest horizontal line indicate a first fitness cycle (e.g., fatigue cycle), measurements between the two horizontal lines indicate a second fitness cycle (e.g., performance cycle), and measurements above the highest horizontal line indicate a third fitness cycle (e.g., recovery cycle).

Figure 15:
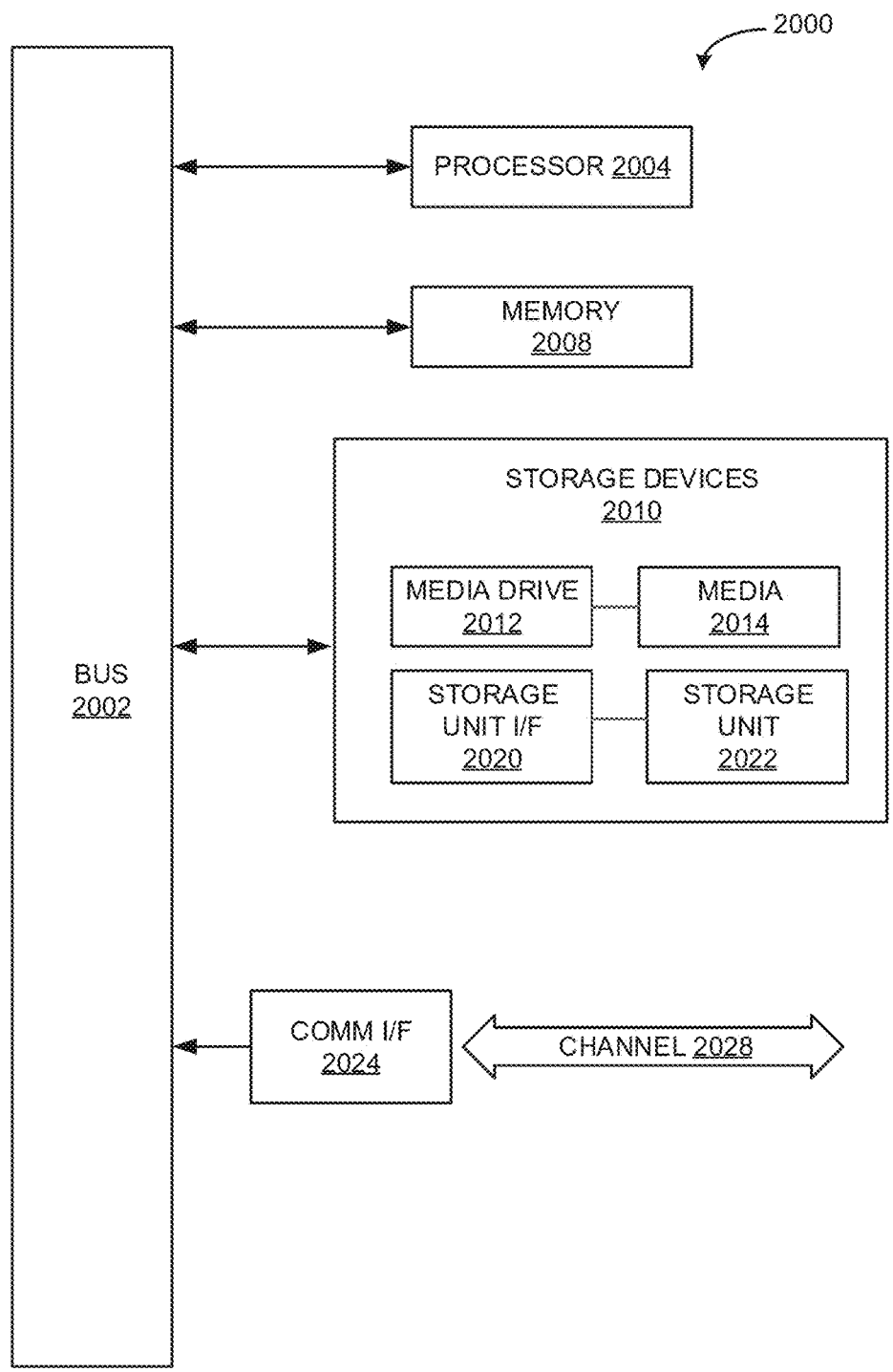
FIG. 15 illustrates an example computing module that may be used to implement various features of the technology disclosed herein.

FIG. 15 illustrates an example computing module that may be used to implement various features of the systems and methods for estimating sky probes disclosed herein. As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 15. Various embodiments are described in terms of this example-computing module 2000. After reading this description, it will become apparent to a person skilled in the relevant art how to implement the application using other computing modules or architectures.

Referring now to FIG. 15, computing module 2000 may represent, for example, computing or processing capabilities found within desktop, laptop, notebook, and tablet computers; hand-held computing devices (tablets, PDA's, smart phones, cell phones, palmtops, etc.); mainframes, supercomputers, workstations or servers; or any other type of special-purpose or general-purpose computing devices as may be desirable or appropriate for a given application or environment. Computing module 2000 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 2000 might include, for example, one or more processors, controllers, control modules, or other processing devices, such as a processor 2004. Processor 2004 might be implemented using a general-purpose or special-purpose processing engine such as, for example, a microprocessor, controller, or other control logic. In the illustrated example, processor 2004 is connected to a bus 2002, although any communication medium can be used to facilitate interaction with other components of computing module 2000 or to communicate externally.

Computing module 2000 might also include one or more memory modules, simply referred to herein as main memory 2008. For example, preferably random access memory (RAM) or other dynamic memory, might be used for storing information and instructions to be executed by processor 2004. Main memory 2008 might also be used for storing temporary variables or other intermediate information during execution of instructions to be executed by processor 2004. Computing module 2000 might likewise include a read only memory ("ROM") or other static storage device coupled to bus 2002 for storing static information and instructions for processor 2004.

The computing module 2000 might also include one or more various forms of information storage mechanism 2010, which might include, for example, a media drive 2012 and a storage unit interface 2020. The media drive 2012 might include a drive or other mechanism to support fixed or removable storage media 2014. For example, a hard disk drive, a solid state drive, a magnetic tape drive, an optical disk drive, a CD, DVD, or Blu-ray drive (R or RW), or other removable or fixed media drive might be provided. Accordingly, storage media 2014 might include, for example, a hard disk, a solid state drive, magnetic tape, cartridge, optical disk, a CD, DVD, Blu-ray or other fixed or removable medium that is read by, written to or accessed by media drive 2012. As these examples illustrate, the storage media 2014 can include a computer usable storage medium having stored therein computer software or data.

In alternative embodiments, information storage mechanism 2010 might include other similar instrumentalities for allowing computer programs or other instructions or data to be loaded into computing module 2000. Such instrumentalities might include, for example, a fixed or removable storage unit 2022 and an interface 2020. Examples of such storage units 2022 and interfaces 2020 can include a program cartridge and cartridge interface, a removable memory (for example, a flash memory or other removable memory module) and memory slot, a PCMCIA slot and card, and other fixed or removable storage units 2022 and interfaces 2020 that allow software and data to be transferred from the storage unit 2022 to computing module 2000.

Computing module 2000 might also include a communications interface 2024. Communications interface 2024 might be used to allow software and data to be transferred between computing module 2000 and external devices. Examples of communications interface 2024 might include a modem or softmodem, a network interface (such as an Ethernet, network interface card, WiMedia, IEEE 802.XX or other interface), a communications port (such as for example, a USB port, IR port, RS232 port BLUETOOTH® interface, or other port), or other communications interface. Software and data transferred via communications interface 2024 might typically be carried on signals, which can be electronic, electromagnetic (which includes optical) or other signals capable of being exchanged by a given communications interface 2024. These signals might be provided to communications interface 2024 via a channel 2028. This channel 2028 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 2008, storage unit 2020, media 2014, and channel 2028. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 2000 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present disclosure should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A system for providing a user a training load schedule, comprising:
a pair of earphones comprising:
speakers;
a processor;
a heartrate sensor electrically coupled to processor; and
a motion sensor electrically coupled to the processor, wherein the processor is configured to process electronic input signals from the motion sensor and the heartrate sensor; and
a non-transitory computer-readable medium operatively coupled to at least one of one or more processors and having instructions stored thereon that, when executed by at least one of the one or more processors, cause the system to:
display on a display an initial load schedule stored in a memory to the user;
calculate a fatigue level of the user based on signals generated by the heart rate sensor;
modify the initial load schedule based on the calculated fatigue level to create a dynamic load schedule for the user; and
display on the display the dynamic load schedule to the user.

2. The system of claim 1, further comprising: a memory storing the initial load schedule and the dynamic load schedule, and wherein the dynamic load schedule is associated with an event taking place on a future date.

3. The system of claim 1, wherein the displayed initial load schedule comprises at least one of a recommended daily activity level and a recommended fatigue level.

4. The system of claim 3, wherein the initial load schedule and the dynamic load schedule are displayed on a calendar using at least one of a color-coding representation and a numerical representation.

5. The system of claim 1, wherein the instructions, when executed by at least one of the one or more processors, further cause the system to:
after displaying the dynamic load schedule, calculate a second fatigue level of the user based on signals generated by the heart rate sensor;
modify the dynamic load schedule based on the second fatigue level;
display on the display the modified dynamic load schedule to the user.

6. The system of claim 1, wherein the instructions, when executed by at least one of the one or more processors, further cause the system to:
receive an external dynamic load schedule;
compare the dynamic load schedule to the external dynamic load schedule; and
display on the display the comparison of the dynamic load schedule to the external dynamic load schedule.

7. The system of claim 6, wherein the external dynamic load schedule is associated with a second user.

8. The system of claim 6, wherein the external dynamic load schedule is a past dynamic load schedule of the user that is associated with a past event.

9. The system of claim 1, wherein the heartrate sensor is an optical heartrate sensor protruding from a side of the earphone proximal to an interior side of a user's ear when the earphone is worn, and wherein the optical heartrate sensor is configured to measure the user's blood flow and to output an electrical signal representative of this measurement to the earphones processor.

10. The system of claim 1, wherein the instructions, when executed by at least one of the one or more processors, further causes the system to calculate a heart rate variability based on signals received from the heartrate sensor, and wherein the fatigue level is calculated based on the calculated heart rate variability.

11. A method for providing a user a training load schedule using earphones with biometric sensors, comprising:
- monitoring a movement of a user based on electrical signals generated by a motion sensor of the earphones;
- displaying on a display an initial load schedule stored in a memory to the user;
- calculating a fatigue level of the user based on signals generated by a heart rate sensor of the earphones;
- one or more processors modifying the initial load schedule based on the calculated fatigue level to create a dynamic load schedule for the user; and
- displaying on the display the dynamic load schedule to the user.

12. The method of claim 11, further comprising: the one or more processors determining if the user complies with the dynamic load schedule by monitoring a movement of the user based on electrical signals generated by a motion sensor of the earphones.

13. The method of claim 11, further comprising: storing the initial load schedule and the dynamic load schedule in a memory, and wherein the dynamic load schedule is associated with an event taking place on a future date.

14. The method of claim 11, wherein the displayed initial load schedule comprises at least one of a recommended daily activity level and a recommended fatigue level.

15. The method of claim 14, wherein the initial load schedule and the dynamic load schedule are displayed on a calendar using at least one of a color-coding representation and a numerical representation.

16. The method of claim 11, further comprising the one or more processors:
- after displaying the dynamic load schedule, calculating a second fatigue level of the user based on signals generated by the heart rate sensor;
- modifying the dynamic load schedule based on the second fatigue level;
- displaying on the display the modified dynamic load schedule to the user.

17. The method of claim 1, further comprising the one or more processors:
- receiving an external dynamic load schedule;
- comparing the dynamic load schedule to the external dynamic load schedule; and
- displaying on the display the comparison of the dynamic load schedule to the external dynamic load schedule.

18. The method of claim 17, wherein the external dynamic load schedule is associated with a second user.

19. The method of claim 17, wherein the external dynamic load schedule is a past dynamic load schedule of the user that is associated with a past event.

20. The method of claim 11, wherein the heartrate sensor is an optical heartrate sensor protruding from a side of the earphone proximal to an interior side of a user's ear when the earphone is worn, and wherein the optical heartrate sensor is configured to measure the user's blood flow and to output an electrical signal representative of this measurement to a processor of the earphones.

21. The method of claim 11, further comprising: calculating a heart rate variability based on signals received from the heartrate sensor, and wherein the fatigue level is calculated based on the calculated heart rate variability.

* * * * *